United States Patent
Ngo et al.

(10) Patent No.: US 9,345,602 B2
(45) Date of Patent: May 24, 2016

(54) PROCESSES FOR MAKING CRUSH RECOVERABLE POLYMER SCAFFOLDS

(75) Inventors: Michael H. Ngo, San Jose, CA (US);
Mikael Trollsas, San Jose, CA (US);
John E. Papp, Temecula, CA (US);
Hung T. Nguyen, San Diego, CA (US);
Dudley Jayasinghe, Murietta, CA (US);
Ron Farnbach, Temecula, CA (US);
Gregory C. Orr, Escondido, CA (US);
Joshua Takeshi Smith, Campbell, CA (US); Yongjin Xie, Cupertino, CA (US);
Yu-Chun Ku, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 671 days.

(21) Appl. No.: 13/090,164

(22) Filed: Apr. 19, 2011

(65) Prior Publication Data
US 2012/0073733 A1   Mar. 29, 2012

Related U.S. Application Data

(63) Continuation-in-part of application No. 13/015,474, filed on Jan. 27, 2011, and a continuation-in-part of application No. 13/015,488, filed on Jan. 27, 2011.

(60) Provisional application No. 61/385,891, filed on Sep. 23, 2010, provisional application No. 61/385,902, filed on Sep. 23, 2010.

(51) Int. Cl.
*B29C 65/02* (2006.01)
*A61F 2/915* (2013.01)
(Continued)

(52) U.S. Cl.
CPC ............... *A61F 2/915* (2013.01); *A61F 2/958* (2013.01); *B29C 55/26* (2013.01); *A61F 2002/91575* (2013.01); *A61F 2002/9522* (2013.01);
(Continued)

(58) Field of Classification Search
CPC ..................... B29C 66/3046; B29C 2791/009
USPC ..................................... 264/280, 400
See application file for complete search history.

(56) References Cited

U.S. PATENT DOCUMENTS

| 5,925,061 A | 7/1999 | Ogi et al. |
| 6,045,568 A | 4/2000 | Igaki et al. |

(Continued)

FOREIGN PATENT DOCUMENTS

| EP | 1 679 095 | 7/2006 |
| WO | WO 2007/146354 | 12/2007 |
| WO | WO2010/151497 | 12/2010 |

OTHER PUBLICATIONS

International Search Report for PCT/US2012/029556, mailed Jul. 30, 2012, 5 pgs.
(Continued)

*Primary Examiner* — Christina Johnson
*Assistant Examiner* — Xue Liu
(74) *Attorney, Agent, or Firm* — Squire Patton Boggs (US) LLP

(57) ABSTRACT

Methods for making scaffolds for delivery via a balloon catheter are described. The scaffold, after being deployed by the balloon, provides a crush recovery of about 90% after the diameter of the scaffold has been pinched or crushed by 50%. The scaffold structure has patterns that include an asymmetric or symmetric closed cell, and links connecting such closed cells.

19 Claims, 16 Drawing Sheets

(51) Int. Cl.
*A61F 2/958* (2013.01)
*B29C 55/26* (2006.01)
*A61F 2/95* (2013.01)
*B29L 31/00* (2006.01)

(52) U.S. Cl.
CPC . *A61F2002/9583* (2013.01); *A61F 2210/0071* (2013.01); *A61F 2230/0054* (2013.01); *B29C 2793/0009* (2013.01); *B29L 2031/753* (2013.01); *Y10T 156/1002* (2015.01)

(56) References Cited

U.S. PATENT DOCUMENTS

| | | | |
|---|---|---|---|
| 6,231,598 | B1 | 5/2001 | Berry et al. |
| 7,498,042 | B2 | 3/2009 | Igaki et al. |
| 2001/0044652 | A1 | 11/2001 | Moore |
| 2002/0013616 | A1 | 1/2002 | Carter et al. |
| 2002/0198558 | A1 | 12/2002 | Briscoe et al. |
| 2002/0198588 | A1 | 12/2002 | Armstrong et al. |
| 2006/0020324 | A1* | 1/2006 | Schmid et al. ............ 623/1.16 |
| 2006/0106453 | A1 | 5/2006 | Sirhan et al. |
| 2006/0271170 | A1 | 11/2006 | Gale et al. |
| 2007/0260302 | A1 | 11/2007 | Igaki |
| 2007/0282428 | A1 | 12/2007 | Igaki |
| 2007/0282433 | A1 | 12/2007 | Limon et al. |
| 2008/0275537 | A1 | 11/2008 | Limon et al. |
| 2009/0157160 | A1* | 6/2009 | Van Der Leest et al. .... 623/1.11 |
| 2009/0163989 | A1 | 6/2009 | Contiliano et al. |
| 2010/0004734 | A1 | 1/2010 | Ramzipoor et al. |
| 2010/0244329 | A1 | 9/2010 | Hossainy et al. |
| 2010/0298926 | A1 | 11/2010 | Igaki |
| 2011/0057356 | A1* | 3/2011 | Jow ............................ 264/400 |
| 2011/0066222 | A1 | 3/2011 | Wang et al. |

OTHER PUBLICATIONS

International Search Report for PCT/US2011/023036, mailed May 21, 2011, 5 pgs.
Daisuke Yoshino et al., "Design and Evaluation of Self-Expanding Stents Suitable for Diverse Clinical Manifestation Based on Mechanical Engineering", Intech, pp. 182-207 (2012).
Duering et al., "A comparison of balloon-and self-expanding stents", Min. Invas. Ther. & Allied Technol. pp. 173-178 (2002).
Duering et al., "An overview of superelastic stent design", Min. Invas. Ther. & Allied Technol. pp. 235-246 (2000).
Lachowitzer "Testing Radial Strength and Stiffness Using Segmental Compression" ASTM International (2004).
Yang Jie et al., "Formula for Elastic Radial Stiffness of the Tubular Vascular Stent" IFMBE Proceedings 31, pp. 1435-1438 (2010).

* cited by examiner

| Attribute | FIGS. 4, 5 and 6A | Scaffold examples having crush recovery and reduced crimp profile | | |
|---|---|---|---|---|
| | | V2 | V23/008 | V23/014 |
| Total length (mm) | - | 36 | 38 | 38 |
| Number of crowns | - | 9 | 9 | 9 |
| Number of links | - | 3 | 3 | 3 |
| wall thickness (in) | 235 | .008 | .008 | .014 |
| OD (mm) | - | 7 | 9 | 9 |
| Strut width (in) | 361 | 0.0085 | 0.011 | 0.011 |
| Crown width (in) | 362 | 0.0085 | 0.011 | 0.011 |
| Link width (in) | 363 | 0.007 | 0.006 | 0.006 |
| Strut length (in) | 364 | 0.071 | 0.081 | 0.081 |
| Ring height (in) | 365 | 0.057 | 0.052 | 0.052 |
| angle (deg.) | 366 | 65 | 100 | 100 |
| angle (deg.) | 367 | 67 | 95 | 95 |
| angle (deg.) | 368 | 59 | 104 | 104 |
| angle (deg.) | 368 | 57 | 104 | 104 |
| crown radius (in) | 369 | 0.0067 | 0.006 | 0.006 |
| crown radius (in) | 370 | 0.0152 | 0.017 | 0.017 |
| crown radius (in) | 371 | 0.0078 | 0.008 | 0.008 |
| crown radius (in) | 372 | 0.0163 | 0.017 | 0.017 |
| crown radius (in) | 373 | 0.0081 | 0.0081 | 0.0081 |
| crown radius (in) | 374 | 0.0166 | 0.015 | 0.015 |
| Range of Radial Strength (N/mm) | - | 0.30-0.45 | 0.30-0.45 | 0.45-0.65 |
| Range of Radial Stiffness (N/mm) | - | 0.50-0.70 | 0.50-0.70 | 0.90-1.10 |
| Range of Crush Recovery (%) at 50% pinching | - | 87-95 | 87-95 | 80-85 |

FIG. 7A

| Attribute | FIGS. 3, 4 & 6B | Scaffold example having crush recovery and reduced crimp profile ("V59") |
|---|---|---|
| pre-crimp diameter (mm) | - | 8 |
| scaffold length (mm) | - | 35.96 |
| number of rings | - | 16 |
| wall thickness (in) | 235 | 0.011 |
| mid strut width (in) | 261 | 0.0116 |
| inner radii (in) | 262 | 0.00025 |
| outer radii (in) | 263 | 0.01325 |
| link width (in) | 264 | 0.0115 |
| ring height (in) | 265 | 0.0589 |
| strut lenght (in) | 266 | 0.0857 |
| angle (deg) | 267 | 101 |
| angle (deg) | 268 | 105 |
| angle (deg) | 269 | 98 |
| no. of struts per ring | - | 16 |
| number of links connecting ring pairs | - | 4 |

FIG. 7B

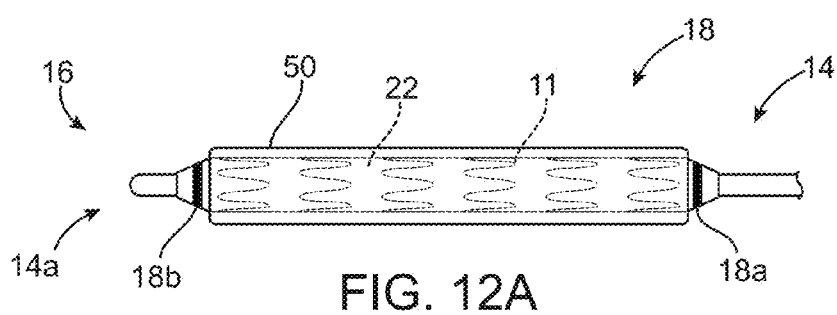
FIG. 12A
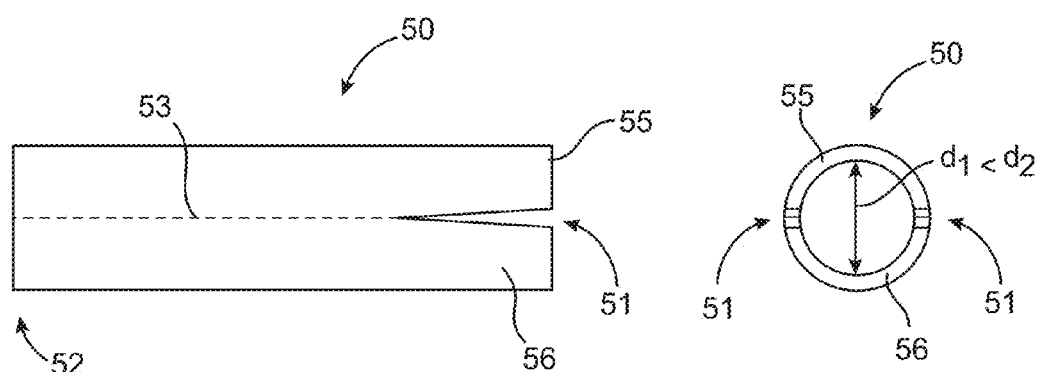
FIG. 12B
FIG. 12C

PROCESSES FOR MAKING CRUSH RECOVERABLE POLYMER SCAFFOLDS

FIELD OF THE INVENTION

The present invention relates to drug-eluting medical devices; more particularly, this invention relates to polymeric scaffolds that are expanded by a delivery balloon.

PRIORITY CLAIM

This application claims priority as a continuation-in-part of U.S. application Ser. No. 13/015,474 filed Jan. 27, 2011 and U.S. application Ser. No. 13/015,488 filed Jan. 27, 2011. This application also claims priority to U.S. provisional application No. 61/385,891 filed on Sep. 23, 2010, and U.S. provisional application No. 61/385,902 filed Sep. 23, 2010.

BACKGROUND OF THE INVENTION

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial yield strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial yield strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal additional force is required to cause major deformation.

Even before the radial yield strength is exceeded there may be permanent deformation in the stent following radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-stent length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries, e.g., iliac, femoral, popliteal, renal and subclavian arteries, however, must be capable of sustaining both radial forces and crushing or pinching loads. These stent types are implanted in vessels that are closer to the surface of the body. Because these stents are close to the surface of the body, they are particularly vulnerable to crushing or pinching loads, which can partially or completely collapse the stent and thereby block fluid flow in the vessel.

As compared to a coronary stent, which is designed to counteract primarily radial loads, a peripheral stent must take into account the significant differences between pinching or crushing loads and radial loads, as documented in Duerig, Tolomeo, Wholey, Overview of superelastic stent Design, Min Invas Ther & Allied Technol 9(3/4), pp. 235-246 (2000) and Stoeckel, Pelton, Duerig, *Self-Expanding Nitinol Stents—Material and Design Considerations*, European Radiology (2003). The corresponding crushing and radial stiffness properties of the stent also can vary dramatically. As such, a stent that possesses a certain degree of radial stiffness does not, generally speaking, also indicate the degree of pinching stiffness possessed by the stent. The two stiffness properties are not the same, or even similar.

The amount of cross-sectional crush during walking expected for a peripheral stent implanted within the femoral artery has been estimated to be about 5.8+/−7%, 6.5+/−4.9% and 5.1+/−6.4% at the top, middle and bottom portions of the femoral artery in older patients and 2.5+/−7.7%, −0.8+/−9.4% and −1.5+/−10.5% for younger patients. These crush estimates can correspond to times when the patient is walking. Significant more crush could occur occasionally by external forces. Other considerations for peripheral stents are the degree of bending and axial compression the stent can withstand without mechanical loss of strength/stiffness. As compared to coronary stents, a peripheral stent usually has lengths of between about 20 and 200 mm when implanted in the superficial femoral artery, as an example. As such, the stent must be flexible enough to withstand axial compression and bending loading without failure. The amount of bending and axial compression expected has been studied and reported in Nikanorov, Alexander, M. D. et al., *Assessment of self-expanding Nitinol stent deformation after chronic implantation into the superficial femoral artery*.

To date the most commonly used type of peripheral stent are self-expanding stents made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided*?, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF.

Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel. However, the prior art has concluded that plastically deformed stents, once collapsed, pinched or crushed in a peripheral artery will remain so, permanently blocking the vessel. The prior art has concluded, therefore, that plastically deformed stents pose an undesirable condition to the patient and should not be used to treat peripheral blood vessels.

A polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, as opposed to a metal stent, is intended to remain in the body for only a limited period of time. The scaffold is made from a biodegradable or bioerodable polymer. In many treatment applications, the presence of a stent in a body may be necessary for a limited period of time until its intended function of, for example, maintaining vascular patency and/or drug delivery is accomplished. Moreover, it is believed that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bio-bioresorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Moreover, it is recognized that the state of the art in medical device-related balloon fabrication, e.g., non-compliant balloons for scaffold deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric scaffold. One difference, for example, is the propensity for fracture or cracks to develop in a polymer scaffold. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a scaffold to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

Processing steps performed on, and design changes made to a metal stent that have not typically raised concerns, or required careful attention to unanticipated changes in the average mechanical properties of the material, therefore, may not also apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping? As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

The present inventors recognize, therefore, that, whereas inferences previously accepted in the art for stent validation or feasibility when an isotropic and ductile metallic material was used, those inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is being crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped onto, and when later deployed by a balloon, unfortunately, is not predictable to the same or similar degree as for a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

In addition to meeting the requirements described above, it is desirable for a scaffold to be radiopaque, or fluoroscopically visible under x-rays. Accurate placement is facilitated by real time visualization of the delivery of a scaffold. A cardiologist or interventional radiologist can track the delivery catheter through the patient's vasculature and precisely place the scaffold at the site of a lesion. This is typically accomplished by fluoroscopy or similar x-ray visualization procedures. For a scaffold to be fluoroscopically visible it must be more absorptive of x-rays than the surrounding tissue. Radiopaque materials in a scaffold may allow for its direct visualization. However, a significant shortcoming of a biodegradable polymer scaffold (and polymers generally composed of carbon, hydrogen, oxygen, and nitrogen) is that they are radiolucent with no radiopacity. Biodegradable polymers tend to have x-ray absorption similar to body tissue. One way of addressing this problem is to attach radiopaque markers to structural elements of the scaffold. A radiopaque marker can be disposed within a structural element in such a way that the marker is secured to the structural element. However, the use of stent markers on a polymeric scaffold entails a number of challenges. One challenge relates to the difficulty of insertion of markers. These and related difficulties are discussed in US 2007/0156230.

There is a need to develop a prosthesis for treating peripheral blood vessels that possesses the desirable qualities of a balloon expanded stent, which does not exert residual outward forces on the vessel (as in the case of a self-expanding stent) while, at the same time, being sufficiently resilient to recover from a pinching or crushing load in a peripheral blood vessel, in addition to the other loading events expected within a peripheral blood vessel that are not typically experienced by a coronary scaffold. There is also a need to fabricate such a polymer scaffold so that the prosthesis also is capable of possessing at least a minimum radial strength and stiffness required to support a peripheral blood vessel; a low crossing profile; and a limited presence in the blood vessel. There is also a need for a scaffold that is easily monitored during its pendency using standard imaging techniques, and is capable of high yield production.

SUMMARY OF THE INVENTION

The invention provides processes for making a polymer scaffold suited to address the foregoing needs including high crush recoverability, e.g., at least about 90-95% after a 50% crushing load. The scaffold is cut from a polymer tube and crimped to a balloon. Accordingly, the invention provides processes for making a balloon expandable, plastically deformed scaffold cut from a tube and being suitable for use as a peripheral scaffold. As such, the drawbacks of self-expanding stents can be obviated by practicing the invention.

To date the art has relied on metals or alloys for support and treatment of peripheral blood vessels. As mentioned earlier, once a metallic stent is implanted it remains in the body permanently, which is not desired. A scaffold made from a material that dissolves after it treats an occluded vessel, therefore, would be preferred over a metal stent. A polymer, however, is much softer than a metal. If it will serve as a replacement to metal, a new design approach is needed.

High radial force, small crimped profile and crush recovery is needed in the polymer scaffold. If the material cannot be modified enough to meet these needs, then a modification to the design of the scaffold network of struts is required. There are a few known approaches to increase the radial yield strength. One is to increase the wall thickness and another is to increase the strut width. Both of these modifications, however, will result in greater profile of the device at the crimped state. A small crimped profile of the device and increased stiffness and strength is therefore necessary and heretofore has not been addressed in the art.

As will be appreciated, aspects of a polymer scaffold produced by the processes described herein contradict conclusions that have been previously made in the art concerning the suitability of a balloon-expandable stent, or scaffold for use in peripheral blood vessels. The problems concerning self-expanding stents are known. Therefore a replacement is sought. However, the conventional wisdom is that a balloon expanded stent having sufficient radial strength and stiffness, as opposed to a self-expanding stent, is not a suitable replacement, especially in vessels that will impose high bending and/or crushing forces on the implanted prosthesis.

According to the invention, crush-recoverable polymer scaffolds made by the processes described herein possess a desired radial stiffness and yield strength, fracture toughness and capability of being crimped down to a target delivery diameter that will properly balance three competing design attributes: radial yield strength and stiffness versus fracture toughness, in-vivo performance versus compactness for delivery to a vessel site, and crush recovery versus radial yield strength and stiffness.

Disclosed herein are embodiments of methods for making a scaffold that can effectively balance these competing needs, thereby providing an alternative to prostheses that suffer from chronic outward force. As will be appreciated from the disclosure, various polymer scaffold combinations were fabricated from the inventive methods and tested in order to better understand the characteristics of a scaffold that might address at least the following needs: crush recoverability of the scaffold without sacrificing a desired minimal radial stiffness and strength, recoil, deploy-ability and crimping profile; acute recoil at deployment—the amount of diameter reduction within ½ hour of deployment by the balloon; delivery/deployed profile—i.e., the amount the scaffold could be reduced in size during crimping while maintaining structural integrity; in vitro radial yield strength and radial stiffness; minimize crack formation/propagation/fracture when crimped and expanded by the balloon, or when implanted within a vessel and subjected to a combination of bending, axial compression, radial crush and radial compressive loads; uniformity of deployment of scaffold rings when expanded by the balloon; and adequate pinching/crushing stiffness.

The various attributes of a crush-recoverable scaffold, such as the various ratios of scaffold properties, e.g., strut and link dimensions (as discussed herein) and relationships relating to crush recoverability; acute recoil at deployment; delivery/deployed profile; in vitro radial yield strength and radial stiffness; radial yield strength and stiffness; uniformity of deployment of scaffold rings when expanded by the balloon; and pinching/crushing stiffness that were produced according to the methods described herein are also described in related U.S. application Ser. No. 13/015,474 and Ser. No. 13/015,488, which is considered part of this disclosure.

In one aspect of the invention, a crush recoverable scaffold was crimped from a 7 mm, 8 mm and 9 mm outer diameter to a 2 mm outer diameter and deployed without fracture and/or excessive cracking of struts that are a typical concern when a polymer, especially a brittle polymer like PLLA, is used to form the scaffold structure.

In another aspect of the invention a symmetric, closed cell for a scaffold improves deployment uniformity and reduces fracture problems for a scaffold having crush recoverability.

In another aspect of invention a method for making a medical device including a scaffold crimped to a balloon-catheter includes the steps of biaxially expanding a polymer precursor to form an expanded tube, forming a scaffold from the expanded tube using a laser, crimping the scaffold to a balloon-catheter at a crimping temperature between about 1 to 10 degrees less than the glass transition temperature of the polymer material and fitting a removable sheath over the scaffold immediately following crimping to limit recoil of the crimped scaffold, wherein the crimped scaffold, when deployed, is capable of regaining at least 90% of its diameter after being crushed to at least 75% of its diameter (or crushed by an amount equal to at least about 25% of its diameter).

In another aspect of invention a method for making balloon-expandable medical device for being implanted in a peripheral vessel of the body includes the steps of biaxially expanding a polymer precursor to from an expanded tube, and forming a scaffold from the expanded tube, including forming struts joined at crowns to form rings, a zero angle radius at the crowns, and symmetric closed cells formed by the rings and connecting links connecting the rings, wherein the scaffold is capable of regaining more than 90% of its diameter after being crushed to about 50% of its diameter.

In another aspect of invention a method for crimping a balloon-expandable medical device includes the steps of forming a pre-crimp scaffold, including the steps of biaxially expanding a PLLA precursor to form an expanded tube including the steps of applying a pressure of about 100-120 psi, a heating nozzle rate of about 0.5-0.9 mm/sec and a temperature of about 230-240 Deg Fahrenheit, and using a pico-second laser, forming a scaffold from the expanded tube, including forming struts forming ring structures connected by longitudinal links, where there are no more than four links connecting adjacent rings; and mounting the scaffold to a balloon, including the steps of using a crimping temperature between 5 to 15 degrees less than the glass transition temperature of PLLA, and maintaining an inflated delivery balloon during crimping to support the scaffold during crimping; wherein the scaffold is capable of regaining more than 90% of its diameter after being crushed to about 50% of its diameter.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIGS. 7A and 7B are tables showing examples of scaffold features in accordance with aspects of the disclosure.

FIG. 10A shows the expanded configuration and FIG. 10B shows the location of the radiopaque markers relative to folded struts of the scaffold rings in the crimped configuration.

FIG. 11A shows a cross-section of a scaffold in its un-deformed (unloaded) state and deformed state when subjected to a pinching load (drawn in phantom). FIGS. 11B-11C are models of equivalent half-cylinder shells of different thickness to show the effects of wall thickness on crush-recoverability when a scaffold is subject a pinching load. The spring elements connected to points A and B are included in FIGS. 11B-11C for purposes of illustrating, by way of analogy, the change in % strain energy at the ends of the half-shells (where failure occurs when the scaffold is pinched beyond its recovery point) as compared to the shells themselves as the wall thickness increases.

FIG. 12A shows a scaffold-catheter assembly with a sheath disposed over a scaffold crimped to a balloon. FIGS. 12B-12C show side and frontal views of the sheath of FIG. 12A.

DETAILED DESCRIPTION OF EMBODIMENTS

The disclosure proceeds as follows. First, definitions of terms that may be used during the course of the subsequent disclosure are explained. Next, the methods for making the scaffold are explained with reference, primarily, to two embodiments of a scaffold (see FIGS. 3-7). The disclosure further provides results from testing of scaffold samples made according to the disclosure, either herein or by way of incorporation by reference with related applications.

Figure 3:
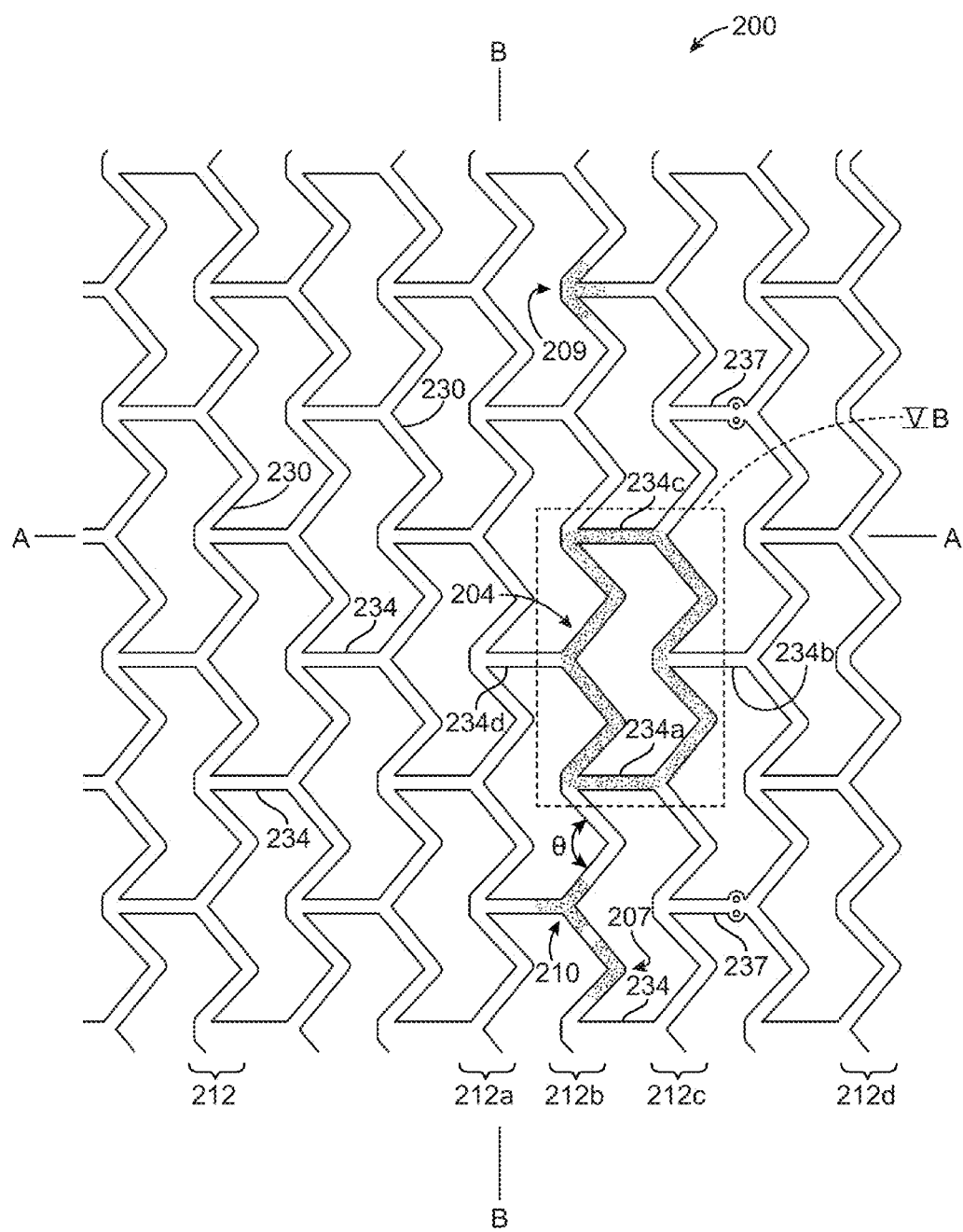
FIG. 3 is a partial planar view of a scaffold pattern according to a first embodiment of a scaffold.
Figure 5:
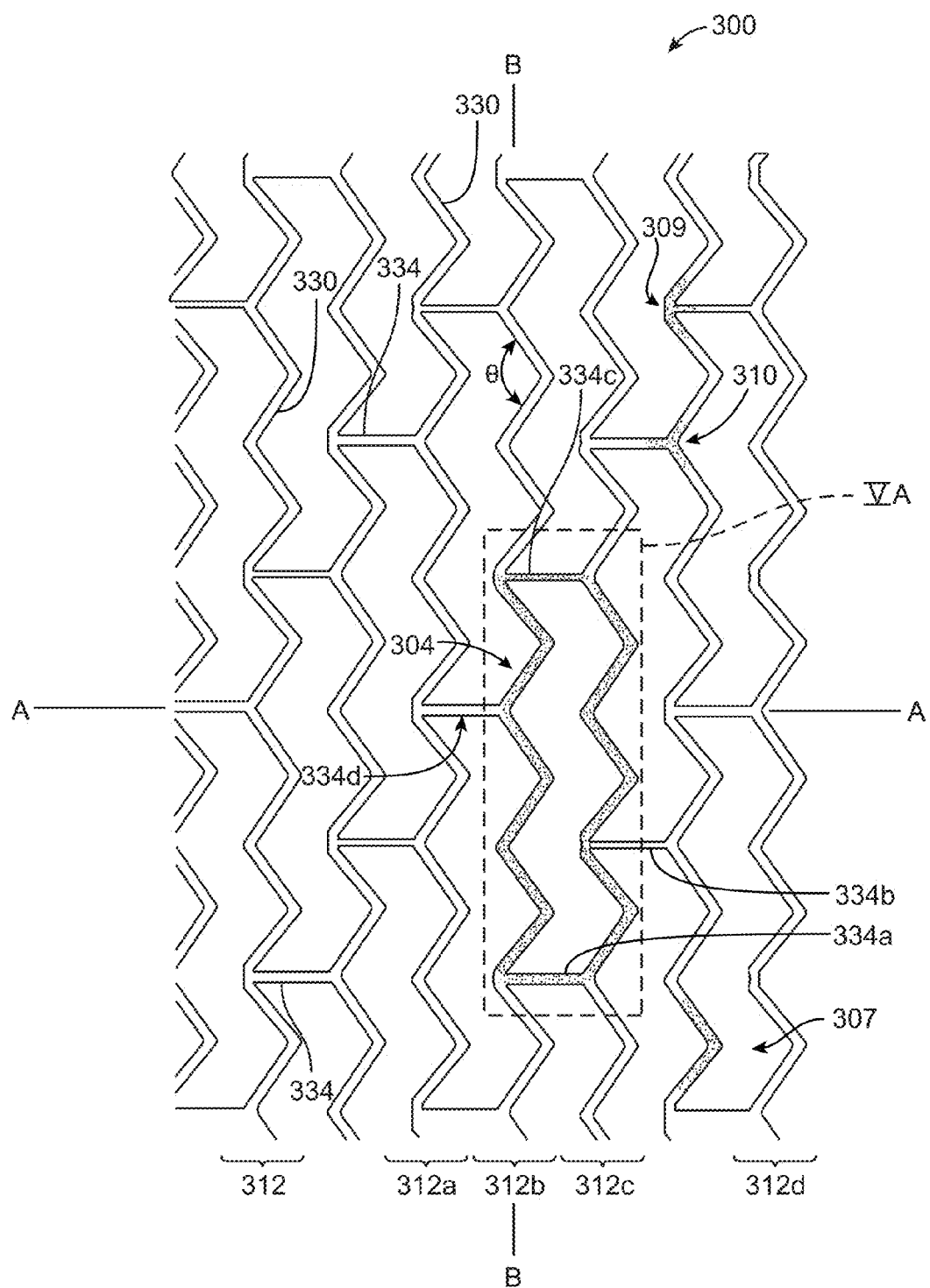
FIG. 5 is a partial planar view of a scaffold pattern according to a second embodiment of a scaffold.

An expansion process for making an expanded polymer tube from an extruded polymer precursor is described, followed by a laser cutting process for forming the scaffold backbone from the expanded tube. Examples of patterns are illustrated in FIGS. 3 and 5. Placement of radiopaque markers is described next, followed by methods for applying a drug-polymer coating to the scaffold. Finally, a crimping process is described. Following the above description, the disclosure explains desirable attributes of scaffolds produced by one or more of the above methods. Finally, test results are discussed including results for scaffold yield strength, stiffness, and crush recovery.

For purposes of this disclosure, the following terms and definitions apply:

"Inflated diameter" or "expanded diameter" refers to the maximum diameter the scaffold attains when its supporting balloon is inflated to expand the scaffold from its crimped configuration to implant the scaffold within a vessel. The inflated diameter may refer to a post-dilation diameter which is beyond the nominal balloon diameter, e.g., a 6.5 mm semi-compliant PEBAX balloon has about a 7.4 mm post-dilation diameter. The scaffold diameter, after attaining its inflated diameter by balloon pressure, will to some degree decrease in diameter due to recoil effects and/or compressive forces imposed by the wall of the vessel after the balloon is removed. For instance, referring to an expansion of the V59 scaffold having the properties in FIG. 6B, when placed on a 6.5 mm PEBAX balloon and the balloon is expanded to a post-dilation condition outside a vessel, the scaffold inner diameter will be about 7.4 mm and about (0.955)×(7.4 mm) before and after, respectively, acute-recoil has occurred. The inflated diameter may be about 1.2 times the average vessel diameter and peripheral vessel sizes typically range from about 4 to 10 mm for purposes of this disclosure.

"Theoretical minimum diameter" means the smallest diameter for a scaffold based on its geometry of strut lengths thickness and widths. A "theoretical minimum diameter" is not defined in terms of a minimum crimped profile for a scaffold or stent that can be later deployed and work properly as a balloon-expanded prosthesis. Rather, it is only a definition defined by the geometry, or minimum volume of space that a device can occupy following a uniform reduction in diameter. As a formula, the "theoretical minimum diameter" ($D_{min}$) may be expressed as follows:

$$D\text{min} = (\Sigma Swi + \Sigma Crj + \Sigma Lwk) * (1/\pi) + 2*WT \qquad (\text{EQ. 3})$$

Where the quantities above are taken from a cross-sectional slice of the scaffold,
$\Sigma Swi$ (i=1 ... n) is the sum of n ring struts having width $Swi$;
$\Sigma Crj$ (j=1 ... m) is the sum of m crown inner radii having radii $Crj$ (times 2);
$\Sigma Lwk$ (k=1 ... p) is the sum of p links having width $Lwk$; and
WT is the scaffold wall thickness.

Figure 8A:
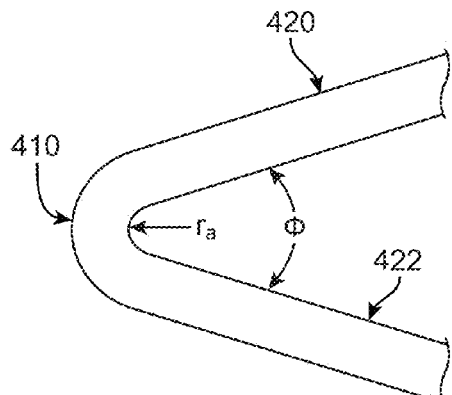
FIG. 8a-8B shows a scaffold crown formation in its expanded and crimped states.

EQ. 3 assumes the width for a folded pair of struts, e.g., struts 420, 422 in FIG. 8A is the same whether measured near the crown 410 or the strut mid width. When the crown is built up more, so that the width is wider there than ring strut mid-width, $Swi$ would be measured by the width at the crown. Also, the minimum space between struts is defined by twice the inner radius of the adjacent crown (or valley), i.e., $Crj$.

For the scaffold dimensions of FIG. 7B the crown width is wider than the strut mid-width. Therefore, using EQ. 3 Dmin is [16*(0.013)+12*(0.0005)+4*(0.0115)]*(1/π)+2*(0.011) =0.1048 in or 2.662 mm (minimum diameter computed at cross-section passing through crowns). If, instead the cross-section were taken at the strut mid width (0.0116 instead of 0.013) EQ. 3 gives 0.0976 in or 2.479 mm.

It should be noted that EQ.3 assumes the struts have essentially a square cross-section. This is the case for the scaffold of FIG. 7B (strut cross-sectional dimension at the crown is 0.011×0.013). For a scaffold having struts with a trapezoidal cross section, e.g., a scaffold cut from a smaller diameter so that the ratio of wall thickness to outer diameter is much higher than in the case of FIG. 1, a more accurate approximation for Dmin would be $(\Sigma Swi+\Sigma Crj+\Sigma Lwk)*(1/\pi)$ since the edges of the struts at the outer surface would abut at Dmin before the surfaces extending over the thickness of a strut abut each other.

The glass transition temperature (referred to herein as "$T_g$") is the temperature at which the amorphous domains of a polymer change from a brittle vitreous state to a solid deformable or ductile state at atmospheric pressure. In other words, $T_g$ corresponds to the temperature where the onset of segmental motion in the chains of the polymer occurs. $T_g$ of a given polymer can be dependent on the heating rate and can be influenced by the thermal history of the polymer. Furthermore, the chemical structure of the polymer heavily influences the glass transition by affecting mobility of polymer chains.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a scaffold or the central axis of a tubular construct. The term "circumferential" refers to the direction along a circumference of the scaffold or tubular construct. The term "radial" refers to a direction, orientation, or line that is perpendicular or substantially perpendicular to the central axis of the scaffold or the central axis of a tubular construct and is sometimes used to describe a circumferential property, i.e. radial yield strength.

The term "crush recovery" is used to describe how the scaffold recovers from a pinch or crush load, while the term "crush resistance" is used to describe the pinch forces required to cause a permanent deformation of a scaffold. A scaffold that does not possess good crush recovery does not substantially return to its original diameter following removal of a crushing force. As noted earlier, a scaffold having a desired radial force can have an unacceptable crush recovery. And a scaffold having a desired crush recovery can have an unacceptable radial force.

Figure 1:
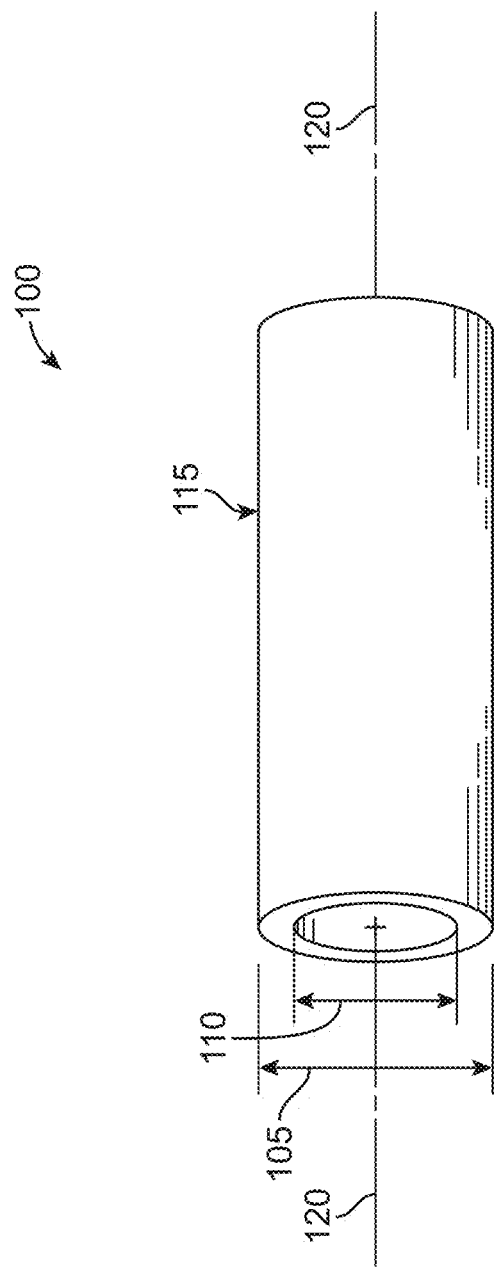
FIG. 1 is a perspective view of a deformed polymer tube. The tube is formed into a scaffold.
Figure 4:
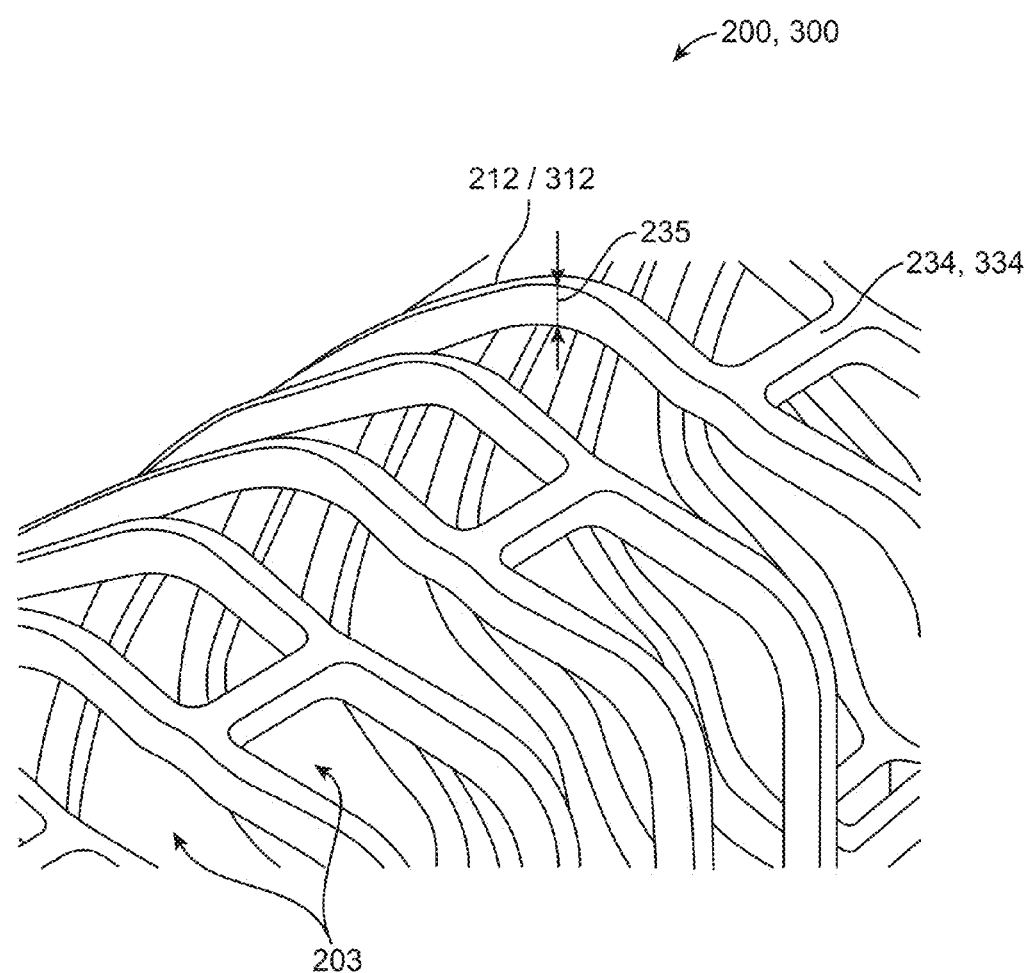
FIG. 4 is a partial perspective view of a scaffold structure.

The polymer scaffold illustrated in FIG. 4 is formed from a poly(L-lactide) ("PLLA") tube 101 as depicted in FIG. 1. The process for forming tube 101 begins with extrusion of a tube precursor. Raw PLLA resin material heated above the melt temperature of the polymer is then extruded through a die at a preferred extrusion temperature of 450 Deg. Fahrenheit. Further details of this step of the process are described in US 2011/0066222 (hereinafter the '222 publ.). A carefully controlled radial and axial expansion of the formed precursor, preferably using a form of blow-molding, follows. This expansion process is employed to produce desired mechanical properties of the scaffold, starting with the precursor. The desirable properties include dimensional and morphological uniformity, e.g., crystallinity, wall thickness and "roundness", yield strength, stiffness and fracture toughness. The resulting tube 101 is then formed into a scaffold using a laser cutting process.

Expansion of the precursor is undertaken using carefully controlled parameters including pressure, rate and temperature during the expansion of the precursor. Expansion preferably occurs in both the axial and radial direction by prescribed amounts to achieve desired results. The PLLA precursor is heated above the PLLA glass transition temperature (i.e., 60-70 degrees C.) but below the melt temperature (165-175 degrees C.), preferably, around 110-120 degrees C.

The preferred blow molding process deforms the precursor progressively at a predetermined longitudinal speed along the longitudinal axis of the precursor. The tube deformation process is intended to orient polymer chains in radial and/or biaxial directions. As mentioned above, the orientation or deformation causing re-alignment is performed according to a precise selection of processing parameters, e.g. pressure, heat (i.e., temperature), deformation rate, to affect material crystallinity and type of crystalline formation during the deformation process.

In an alternative embodiment the tube may be made of poly(L-lactide-co-glycolide), poly(D-lactide-co-glycolide) ("PLGA"), polycaprolactone, ("PCL"), and other suitable semi-crystalline copolymers or blends of these polymers. Rubber toughen material could also be achieved by using block copolymers or polymer blends of the above materials in combination with low $T_g$ materials such as polycprolactone, polyethyleneglycol and polydioxanone. Alternatively multi-layered structures could be extruded. Material choices may be limited when taking into account the complex loading environment associated with many peripheral vessel locations, particularly those located close to limbs.

The degree of radial expansion that the polymer tube undergoes can partially characterize the degree of induced circumferential molecular and crystal orientation as well as strength in a circumferential direction. The degree of radial expansion is quantified by a radial expansion ("RE") ratio, defined as RE Ratio=(Inside Diameter of Expanded Tube)/(Original Inside Diameter of the tube). The RE ratio can also be expressed as a percentage, defined as RE %=(RE ratio−1).times.100%. The degree of axial extension that the polymer tube undergoes can partially characterize induced axial molecular or crystal orientation as well as strength in an axial direction. The degree of axial extension is quantified by an axial extension ("AE") ratio, defined as AE Ratio=(Length of Extended Tube)/(Original Length of the Tube). The AE ratio can also be expressed as a percentage, defined as AE %=(AE ratio−1).times.100%.

Blow molding includes first positioning the tube precursor (or precursor) in a hollow cylindrical member or mold. The mold controls the degree of radial deformation of the precursor by limiting the deformation of the outside diameter or surface of the precursor to the inside diameter of the mold. While in the mold, the precursor temperature is above $T_g$ of PLLA to facilitate deformation. This temperature is a processing parameter referred to as the "expansion temperature" or "process temperature." The heating to the expansion temperature can be achieved by heating a gas to the expansion temperature and discharging the heated gas onto an exterior surface of the mold containing the precursor.

While in the mold, one end of the precursor is sealed or blocked. Thus, introduction of gas into the opposite end of the precursor will increase internal fluid pressure relative to ambient pressure in a region between the outer surface of the precursor and the inner surface of the mold. The internal fluid pressure is a processing parameter referred to as the "expansion pressure" or "process pressure." Examples of gas that may be used to create the expansion pressure include without limitation ambient air, substantially pure oxygen, substantially pure nitrogen, and other substantially pure inert gases. In combination with other blow molding process parameters, the expansion pressure affects the rate at which the precursor deforms radially and axially to produce the tube 101 shown in FIG. 1. Blow molding may include pulling one end of the precursor. A tensile force, which is another processing parameter, is applied to one end of the while holding the other end of the precursor stationary.

The radially and axially deformed precursor may then be cooled from above $T_g$ to below $T_g$, either before or after decreasing the pressure and/or decreasing tension. Cooling at a controlled temperature, or rate of temperature drop, helps insure the tube 101 maintains the proper shape, size, and length following radial expansion and axial extension. Slow cooling through a temperature range between $T_m$ and $T_g$ might result in a loss of amorphous chain orientation and cause a decrease in fracture toughness of the finished scaffold. Preferably, though not necessarily, the deformed precursor can be cooled quickly or quenched in relatively cold gas or liquid to a temperature below $T_g$ to maintain chain orientation that was formed during tubing expansion. The deformed precursor after cooling produces the tube 101, which may be then cut to produce the scaffold described in FIGS. 3, 4, 6B and 7B.

Figure 2A:
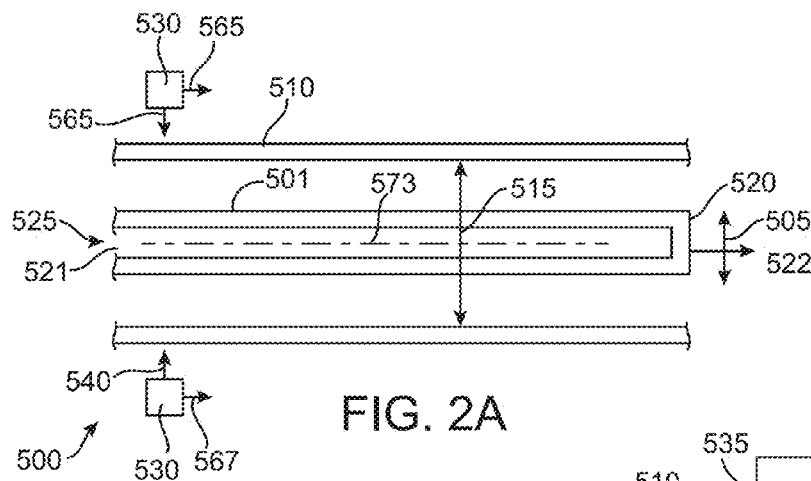
FIGS. 2A-2D are schematic drawings describing a process for radial and axial expansion of a precursor that is formed into the tube of FIG. 1.

FIGS. 2A-2D schematically depicts a molding system 500 for simultaneous radial and axial deformation of a polymer tube. FIG. 2A depicts an axial cross-section of a polymer tube 501 with an undeformed outside diameter 505 positioned within a mold 510. The mold 510 limits the radial deformation of the polymer tube 501 to a diameter 515 corresponding to the inside diameter of the mold 510. The polymer tube 501 is closed at a distal end 520. A gas is conveyed, as indicated by an arrow 525, into an open end 521 of the polymer tube 501 to increase internal fluid pressure within tube 501.

A tensile force 522 is applied to the distal end 520 in an axial direction. In other embodiments, a tensile force is applied at the proximal end 521 and the distal end 520.

Figure 2B:
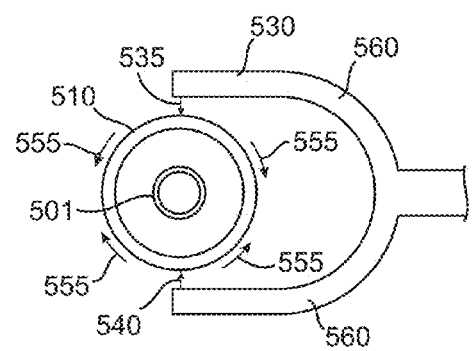

A circular band or segment of the polymer tube 500 is heated by a nozzle 530. The nozzle has fluid ports that direct a heated fluid, such as hot air, at two circumferential locations of the mold 510, as shown by arrows 535 and 540. FIG. 2B depicts a radial cross-section showing the tube 501 within the mold 510, and the nozzle 530 supported by structural members 560. Additional fluid ports can be positioned at other circumferential locations of the mold 510 to facilitate uniform heating around a circumference of the mold 510 and the tube 501. The heated fluid flows around the mold 510, as shown by arrows 555, to heat the mold 510 and the tube 501 to a predetermined temperature above ambient temperature.

The nozzle 530 translates along the longitudinal axis 573 of the mold 510 as shown by arrows 565 and 567. That is, the nozzle 530 moves linearly in a direction parallel to the longitudinal axis 573 of the mold 510. As the nozzle 530 translates along the axis of the mold 510, the tube 501 radially deforms. The combination of elevated temperature of the tube 501, the applied axial tension, and the applied internal pressure cause simultaneous axial and radial deformation of the tube 501, as depicted in FIGS. 2C and 2D.

Figure 2C:
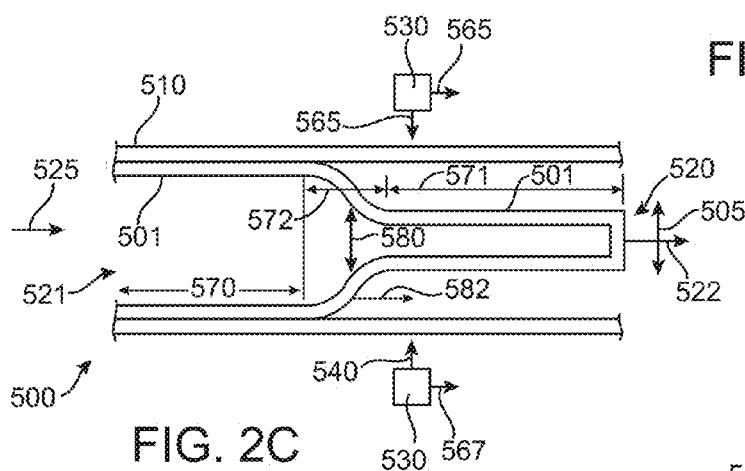

FIG. 2C depicts the system 500 with an undeformed section 571, a deforming section 572, and a deformed section 570 of the polymer tube 501. Each section 570, 571, 572 is circular in the sense that each section extends completely around the central axis 573. The deforming section 572 is in the process of deforming in a radial direction, as shown by arrow 580, and in an axial direction, as shown by arrow 582. The deformed section 570 has already been deformed and has an outside diameter that is the same as the inside diameter of the mold 510.

Figure 2D:
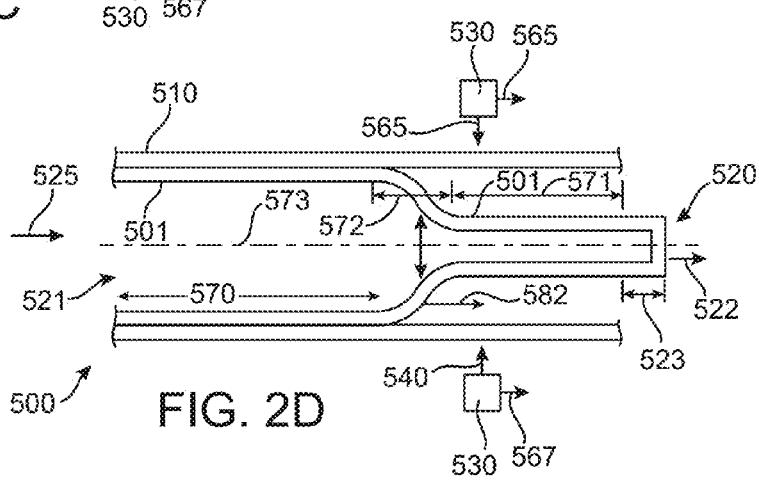

FIG. 2D depicts the system 500 at some time period after FIG. 2C. The deforming section 572 in FIG. 2D is located over a portion of what was an undeformed section in FIG. 2C. Also, the deformed section 570 in FIG. 2D is located over what was the deforming section 572 in FIG. 2C. Thus it will be appreciated that the deforming section 572 propagates linearly along the longitudinal axis 573 in the same general direction 565, 567 that the heat sources 530 are moving.

In FIG. 2D, the deforming section 572 has propagated or shifted by an axial distance 574 from its former position in FIG. 2C. The deformed section 570 has grown longer by the same axial distance 574. Deformation of the tube 501 occurs progressively at a selected longitudinal rate along the longitudinal axis 573 of the tube. Also, the tube 501 has increased in length by a distance 523 compared to FIG. 2C.

Depending on other processing parameters, the speed at which the heat sources or nozzles 530 are linearly translated over the mold 510 may correspond to the longitudinal rate of propagation (also referred to as the axial propagation rate) of the polymer tube 501. Thus, the distance 574 that the heat sources 530 have moved is the same distance 575 that the deformed section 570 has lengthened.

The rate or speed at which the nozzles 530 are linearly translated over the mold 510 is a processing parameter that relates to the amount of time a segment of the polymer tube is heated at the expansion temperature and the uniformity of such heating in the polymer tube segment.

It is to be understood that the tensile force, expansion temperature, and expansion pressure are applied simultaneously to the tube 501 while the nozzle 530 moves linearly at a constant speed over the mold. Again, the "expansion pressure" is the internal fluid pressure in the polymer tube while it is blow molded inside the mold. In FIGS. 2A-2D, the "expansion temperature" is the temperature to which a limited segment of the polymer tube is heated during blow molding. The "limited segment" is the segment of the polymer tube surrounded by the nozzle 530. The "limited segment" may include the deforming section 572. The heating of the polymer tube to the expansion temperature can be achieved by heating a gas to the expansion temperature and discharging the heated gas from the nozzle 530 onto the mold 510 containing the polymer tube.

The processing parameters of the above-described blow molding process include without limitation the tensile force, expansion temperature, the expansion pressure, and nozzle translation rate or linear movement speed. It is expected that the rate at which the tube deforms during blow molding depends at least upon these parameters. The deformation rate has both a radial component, indicated by arrow 580 in FIGS. 2C and 2D, and an axial component, indicated by an arrow 582. It is believed that the radial deformation rate has a greater dependence on the expansion pressure and the axial component has a greater dependence on the translation rate of the heat source along the axis of the tube. It is also expected that the deformation rate is dependant upon the pre-existing morphology of the polymer in the undeformed section 571. Also, since deformation rate is a time dependent process, it is expected to have an effect on the resulting polymer morphology of the deformed tube after blow molding.

The term "morphology" refers to the microstructure of the polymer which maybe characterized, at least in part, by the percent crystallinity of the polymer, the relative size of crystals in the polymer, the degree of uniformity in spatial distribution of crystals in the polymer, and the degree of long range order or preferred orientation of molecules and/or crystals. Morphology may also refer to the degree of phase separation in a rubber-toughened material. The crystallinity percentage refers to the proportion of crystalline regions to amorphous regions in the polymer. Polymer crystals can vary in size and are sometimes geometrically arranged around a nucleus, and such arrangement may be with or without a preferred directional orientation. A polymer crystal may grow outwardly from the nucleus as additional polymer molecules join the ordered arrangement of polymer molecule chains. Such growth may occur along a preferred directional orientation.

Applicant believes that all the above-described processing parameters affect the morphology of the deformed polymer tube 501. As used herein, "deformed tube 501" and "blow molded tube 501" are used interchangeably and refer to the deformed section 570 of the polymer tube 501 of FIGS. 2C and 2D. Without being limited to a particular theory, Applicant believes that increasing the crystallinity percentage will increase the strength of the polymer but also tends to make the polymer brittle and prone to fracture when the crystallinity percentage reaches a certain level. Without being limited to a particular theory, Applicant believes that having a polymer with relatively small crystal size has higher fracture toughness or resistance to fracture. Applicant also believes that having a deformed tube 501 with spatial uniformity in the radial direction, axial direction, and circumferential direction also improves strength and fracture toughness of the stent made from the deformed tube.

It should be noted that the above-described processing parameters are interdependent or coupled to each other. That is, selection of a particular level for one processing parameter affects selection of appropriate levels for the other processing parameters that would result in a combination of radial expansion, axial extension, and polymer morphology that produces a stent with improved functional characteristics such as reduced incidence of strut fractures and reduced recoil. For example, a change in expansion temperature may also change the expansion pressure and nozzle translation rate required to obtain improved stent functionality.

Expansion temperature affects the ability of the polymer to deform (radially and axially) while simultaneously influencing crystal nucleation rate and crystal growth rate, as shown in FIG. 4 of '222 publ. It depicts an exemplary schematic plot of crystallization under quiescent condition, showing crystal nucleation rate ("RN") and the crystal growth rate ("RCG") as a function of temperature. The crystal nucleation rate is the rate at which new crystals are formed and the crystal growth rate is the rate of growth of formed crystals. The exemplary curves for RN and RCG in FIG. 4 of '222 publ. have a curved bell-type shape that is similar to RN and RCG curves for PLLA. The overall rate of quiescent crystallization ("RCO") is the sum of curves RN and RCG.

Quiescent crystallization can occur from a polymer melt, which is to be distinguished from crystallization that occurs solely due to polymer deformation. In general, quiescent crystallization tends to occur in a semi-crystalline polymer at temperatures between $T_g$ and $T_m$ of the polymer. The rate of quiescent crystallization in this range varies with temperature. Near $T_g$, nucleation rate is relatively high and quiescent crystal growth rate is relatively low; thus, the polymer will tend to form small crystals at these temperatures. Near $T_m$, nucleation rate is relatively low and quiescent crystal growth rate is relatively high; thus, the polymer will form large crystals at these temperatures.

As previously indicated, crystallization also occurs due to deformation of the polymer. Deformation stretches long polymer chains and sometimes results in fibrous crystals generally oriented in a particular direction. Deforming a polymer tube made of PLLA by blow molding at a particular expansion temperature above $T_g$ results in a combination of deformation-induced crystallization and temperature-induce crystallization.

As indicated above, the ability of the polymer to deform is dependent on the blow molding temperature ("expansion temperature") as well as being dependant on the applied internal pressure ("expansion pressure") and tensile force. As temperature increases above $T_g$, molecular orientation is more easily induced with applied stress. Also, as temperature approaches $T_m$, quiescent crystal growth rate increases and quiescent nucleation rate decreases. Thus, it will also be appreciated that the above described blow molding process involves complex interaction of the processing parameters all of which simultaneously affect crystallinity percentage, crystal size, uniformity of crystal distribution, and preferred molecular or crystal orientation.

As mentioned earlier, in a preferred embodiment the PLLA tube was made entirely of PLLA. The preferred levels are given below for the blow molding process parameters for a PLLA precursor having an initial (before blow molding) crystallinity percentage of up to about 20% and more narrowly from about 5% to about 15%. Applicants believe the blow molding process parameter levels given below result in a deformed PLLA tube having a crystallinity percentage below 50% and more narrowly from about 30% to about 40%.

Approximate values of the processing conditions for a preferred embodiment are depicted below. The processing conditions provided TABLE 1 were used to produce tube 101 from the precursor. The tube 101 was then formed into the scaffold described in FIGS. 3-7.

TABLE 1

Preferred processing conditions for producing tube 101

| Processing parameters | Expansion parameters used to form a tube 101 from an extruded PLLA precursor |
|---|---|
| temperature (Deg. F.) | 230-240 |
| pressure (psi) | 100-120 |
| nozzle rate (mm/sec) | 0.48-0.88 |
| % RA | 400 |
| % RE | 40-50 |
| Degree of Crystallinity | 40-50% |

After expansion, the tube 101 may be subjected to an extended period of elevated temperature. In one embodiment, a PLLA tube 101 is subjected to a temperature of between about 40-50 Deg Celsius or about 47 Deg Celsius before laser-cutting the tube to form the scaffold. This step would occur after the expanded tube is quenched. The subsequent, prolonged exposure to an elevated temperature, which may be included in the process, is intended to induce relaxation of internal stresses in the deformed precursor far more slowly than a typical annealing process. The process may be thought of as a "cold crystallization process".

In a preferred embodiment a PLLA tube (or scaffold after laser cutting of the tube) is subjected to a temperature of about 47 Deg over a four week period. It is believed that the process produces enhanced strength and stiffness properties. Other temperature ranges may be used. Conceivably, a higher temperature will bring about the annealing process more quickly. However, it is preferred to not raise the temperature too far above about 50 Deg Celsius as this will start to cause excessive and undesired movement or re-ordering of polymer chains. For PLLA it was found that cold sterilization at 37 Deg Celsius did not produce any noticeable differences.

Following expansion the tube 101 is fabricated into a scaffold by laser machining. Material is removed from selected regions of the tube which results in formation of the patterns depicted herein. A laser beam is scanned over the surface of the tube 101 resulting in removal of a trench or kerf extending all the way through a wall of the tubing, either in one pass or two passes with the laser. In a presently preferred embodiment of a scaffold having an average wall thickness of about 0.011 inches two passes are made to form the scaffold pattern. After the second pass, the starting and ending points of where the laser's kerf meet, the region surrounded by the kerf drops out or is removed by an assisting gas. A preferred set of laser parameters for the scaffold depicted in FIGS. 3-7 is provided in TABLE 2, below. Other details are found in U.S. application Ser. No. 12/797,950.

TABLE 2

Laser Machining Parameters for a crush recoverable polymer scaffold having a wall thickness of between about .008 in and .014 in:

| | |
|---|---|
| laser type | 515 nm (Trumpf, green light) |
| Tube length (mm) | 80-250 |
| wall thickness (in) | .008-.014 |
| Scaffold length (mm) | 30-120 |
| No. of passes to cut | 1-4 |
| Cutting speed (in/min) | 4-10 |
| Tube outer diameter (mm) | 6-10 |
| Laser spot/beam size (μm) | 10-20 |
| Laser rep rate (kHz) | 5-50 |
| average power (W) | .7-2.0 |
| Helium gas flow (scfh) | 10-30 |

In one embodiment following laser machining a structure having a plurality of struts 230 and links 234 forming a pattern 200 as shown in FIG. 3 (pattern 200 is illustrated in a planar or flattened view) is formed. the pattern shown in FIG. 3 is about that of the scaffold before crimping and after the scaffold is plastically, or irreversibly deformed from its crimped state to its deployed state within a vessel by balloon expansion. The pattern 200 of FIG. 3, therefore, represents a tubular scaffold structure (as partially shown in three dimensional space in FIG. 4), so that an axis A-A is parallel to the central or longitudinal axis of the scaffold. FIG. 4 shows the scaffold in a state prior to crimping or after deployment. As can be seen from FIG. 4, the scaffold comprises an open framework of struts and links that define a generally tubular body.

In a preferred embodiment laser machining includes the step of forming regions in connecting links to hold a radiopaque marker bead, e.g., a platinum bead. The structure for holding marker beads in a preferred embodiment is described in FIGS. 10A-10B and the accompanying text, infra.

The size of the marker bead is proportional to the visibility of the bead when the scaffold is implanted within the body. A marker bead, therefore, is preferably sufficiently large enough so that it can easily be seen using a fluoroscope. A process for placing a radiopaque marker bead in each of the pair of depots 500 in FIG. 10A includes the following steps. A bead is held by a vacuum pick and placed over the depot 500. Then a hand-held mandrel is used to push the bead into the channel formed by the depot. For the scaffold "V59", for example (FIG. 7B), the diameter of the bead (e.g., about 0.009 inches) is less than the wall thickness of the scaffold. As such, the bead may be placed so that it does not protrude beyond the walls of the scaffold. This allows the bead to be easily placed within the depot without the additional step of deforming the malleable bead (so that a flush outer surface is formed with adjacent luminal and abluminal walls of the scaffold). A marker bead process according to one embodiment may therefore include placing the bead within the depot without significantly deforming the bead. The bead may then be secured in place by a coating material, e.g., a drug-polymer layer applied during a coating step for the scaffold.

Following placement of the marker beads in the scaffold, a drug-polymer coating is applied by a spraying and drying process. A spray nozzle is used to apply the coating material. And a dryer is used to apply inter-pass drying of coating. The term "inter-pass drying" means drying, or removing solvent between one, two, three or more spray passes. Preferably between about 13-14 coats are applied to reach 100% of a coating weight for a scaffold. Methods for spraying and drying a scaffold are described in U.S. application Ser. No. 12/554,820. An apparatus and process for removing gases from a solution sprayed onto a scaffold are described in U.S. application Ser. No. 13/039,192. During the spraying step, the scaffold is held on a rotating mandrel designed to minimize the amount of coating defects on the scaffold. Examples of such a mandrel are described in U.S. application Ser. No. 12/752,983.

After the desired coating has been applied and the desired amount of solvent removed, the scaffold is mounted onto a balloon catheter by a crimping process. During crimping there is a precise control of temperature within a specific range for these materials, in relation to their glass transition temperature ($T_g$), to improve the retention force on a balloon without causing adverse effects on the polymer scaffold's yield strength and stiffness properties when it is later expanded by the balloon. Additionally, crimping at below but close to $T_g$ has been found to reduce the instances of cracking of scaffold struts. Processes for crimping a scaffold are described in U.S. application Ser. No. 12/772,116 and U.S. application Ser. No. 12/861,719.

Crimping processes for the "V23" scaffold (FIG. 7A) and "V59" scaffold (FIG. 7B) are summarized in TABLES 3A and 3B. In these example a crimping temperature of between 5-15 degrees below $T_g$, and more preferably about 44-52 and 48 Deg Celsius was used.

TABLE 3A crimping process for the "V23" scaffold

Stage 1 - crimp head closes to .314 in at a speed of .5 inches per second (in/s) then immediately go to Stage 2.
Stage 2 - crimp head closes to .300 in at a speed of .005 in/s and dwells for 30 seconds.
Stage 3 - crimp head closes to .270 in at a speed of .005 in/s and dwells for 30 seconds. Turn stopcock to release pressure from the inflated support balloon catheter.
Stage 4 - crimp head closes to .240 in at a speed of .005 in/s and dwells for 30 seconds.
Stage 5 - crimp head closes to .200 in at a speed of .005 in/s and dwells for 30 seconds.
Stage 6 - crimp head closes to .160 in at a speed of .005 in/s and dwells for 30 seconds. Activate pressurization mode of crimping station to inflate a support balloon with 50 psi to align any misaligned struts between Stage 3 and Stage 5. After dwelling for 30 seconds the crimp head opens, remove the scaffold/support balloon from the crimp head. Remove partially crimped scaffold and place it on the balloon of the balloon catheter ("FG balloon catheter"). Insert this assembly back into the center of the crimp head. Reactivate the crimper.
Stage 7 - crimp head closes to .160 in at a speed of .25 in/s and dwells for 30 seconds.
Stage 8 - crimp head closes to .130 in at a speed of .005 in/s and dwells for 50 seconds. Activate pressurization mode to inflate the FG balloon catheter 50 psi to create pillowing effect to improve scaffold retention and dwell for 50 seconds. Deactivate pressurization mode after 50 seconds have elapsed.
Stage 9 - crimp head closes to .074 in at a speed of .005 in/s and dwells for 150 seconds.

TABLE 3B crimping process for the "V59" scaffold

Stage 1 - crimp head closes to .3543 in at a speed of .3 inches per second (in/s) then immediately go to Stage 2.
Stage 2 - crimp head closes to .270 in at a speed of .005 in/s and dwells for 30 seconds.
Stage 3 - crimp head closes to .210 in at a speed of .005 in/s and dwells for 30 seconds.
Stage 4 - crimp head closes to .160 in at a speed of .005 in/s and dwells for 30 seconds.
Stage 5 - crimp head closes to .130 in at a speed of .005 in/s and dwells for 30 seconds. Activate pressurization mode of crimping station to inflate a support balloon with 50 psi to help re-align any misaligned struts created during Stages 2 and 4. After the 30 second dwell the crimp head opens, remove the scaffold/support balloon from the crimp head. Remove partially crimped scaffold and place it on the balloon of the balloon catheter ("FG balloon catheter"). Insert this assembly back into the center of the crimp head. Reactivate the crimper.
Stage 6 - crimp head closes to .140 in at a speed of .05 in/s and dwells for 5 seconds.
Stage 7 - crimp head closes to .130 in at a speed of .005 in/s and dwells for 30 seconds.
Stage 8 - crimp head closes to .100 in at a speed of .005 in/s and dwells for 30 seconds. Activate pressurization mode to inflate the FG balloon catheter to 50 psi for dwell period.
Stage 9 - crimp head closes to .0625 in at a speed of .005 in/s and dwells for 170 seconds.

Crimp processes similar to TABLES 3A and 3B are provided for V23 in paragraphs [0072] through [0092] in U.S. application Ser. No. 12/861,719. In one embodiment, the crimping process may include the step of maintaining an internal, elevated pressure (above ambient) or slowly bleeding a balloon-pressure valve while the crimping jaws are moving the scaffold diameter from a first to second diameter.

After Stage 9 the scaffold is immediately placed within a restraining sheath to prevent recoil in the scaffold structure following crimping. The sheath is not intended to stay with the Finished Goods (FG) balloon catheter when it is later implanted within a patient. Rather, the sheath is removed before the scaffold-balloon is introduced into the patient's affected vessel lesion.

Examples of sheaths suited for this purpose are described in U.S. application Ser. No. 12/916,349. In the examples given here, various slits, cuts or weakened areas may be pre-formed in the sheath to facilitate a tearing away or removal of the sheath from the scaffold by a health professional, without dislodging the scaffold from the balloon. The removable sheath can have weakened areas preferably designed so that it can be easily removed without applying an excessive pulling force on the crimping scaffold.

Referring to FIGS. 12A-12B, a sheath 50 includes weakened areas 51 and 53 arranged so that a medical professional may remove the sheath by tearing the sheath manually along lines of weaknesses in the sheath. Referring to FIG. 12A, when disposed over the crimped scaffold 22 of the scaffold-catheter assembly 18, the sheath 50 may have a proximal end 52 and distal end 54 located, respectively, near the proximal and distal balloon markers 18a, 18b of the balloon 22 (FIG. 12A). At the distal end 54 there as a pair of opposed v-shaped cuts defining upper and lower pull flaps 55 and 56. The dashed lines 53 indicate the intended tear line when the opposed flaps 55, 56 are manually pulled apart to initiate tearing along the line 53. In one embodiment, the tear lines 53 may also correspond to pre-formed slits, having a depth about half the sheath 50 wall thickness and over the length of the sheath 50. In one embodiment the sheath 50 distal end 54 may extend beyond the scaffold distal end 14a of a distal portion 14 of the scaffold-catheter assembly 18. The distal end flaps 55, 56 may be folded up or over the sheath 50 to make the flaps 55, 56 more easy to grip and pull up and down respectively, so as to avoid longitudinally applied forces on the scaffold surface as the sheath 50 is torn away.

Referring to FIG. 3, the pattern 200 includes longitudinally-spaced rings 212 formed by struts 230. A ring 212 is connected to an adjacent ring by several links 234, each of which extends parallel to axis A-A. In this first embodiment of a scaffold pattern (pattern 200) four links 234 connect the interior ring 212, which refers to a ring having a ring to its left and right in FIG. 3, to each of the two adjacent rings. Thus, ring 212b is connected by four links 234 to ring 212c and four links 234 to ring 212a. Ring 212d is an end ring connected to only the ring to its left in FIG. 3.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200, although in other embodiments a ring with curved struts is contemplated. As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 3). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than a maximum expanded scaffold diameter that the delivery balloon can, or is capable of producing when inflated. According to one embodiment, a pre-crimp diameter is greater than the scaffold expanded diameter, even when the delivery balloon is hyper-inflated, or inflated beyond its maximum use diameter for the balloon-catheter.

Pattern 200 includes four links 237 (two at each end, only one end shown in FIG. 3) having structure formed to receive a radiopaque material in each of a pair of transversely-spaced holes formed by the link 237. These links are constructed in such a manner as to avoid interfering with the folding of struts over the link during crimping, which, as explained in greater detail below, is necessary for a scaffold capable of being crimped to a diameter of about at most Dmin or for a scaffold that when crimped has virtually no space available for a radiopaque marker-holding structure.

A second embodiment of a scaffold structure has the pattern 300 illustrated in FIG. 5. Like the pattern 200, the pattern 300 includes longitudinally-spaced rings 312 formed by struts 330. A ring 312 is connected to an adjacent ring by several links 334, each of which extends parallel to axis A-A.

The description of the structure associated with rings 212, struts 230, links 234, and crowns 207, 209, 210 in connection with FIG. 3, above, also applies to the respective rings 312, struts 330, links 334 and crowns 307, 309 and 310 of the second embodiment, except that in the second embodiment there are only three struts 334 connecting each adjacent pair of rings, rather than four. Thus, in the second embodiment the ring 312b is connected to the ring 312c by only three links 234 and to the ring 312a by only three links 334. A link formed to receive a radiopaque marker, similar to link 237, may be included between 312c and ring 312d.

Figure 6A:
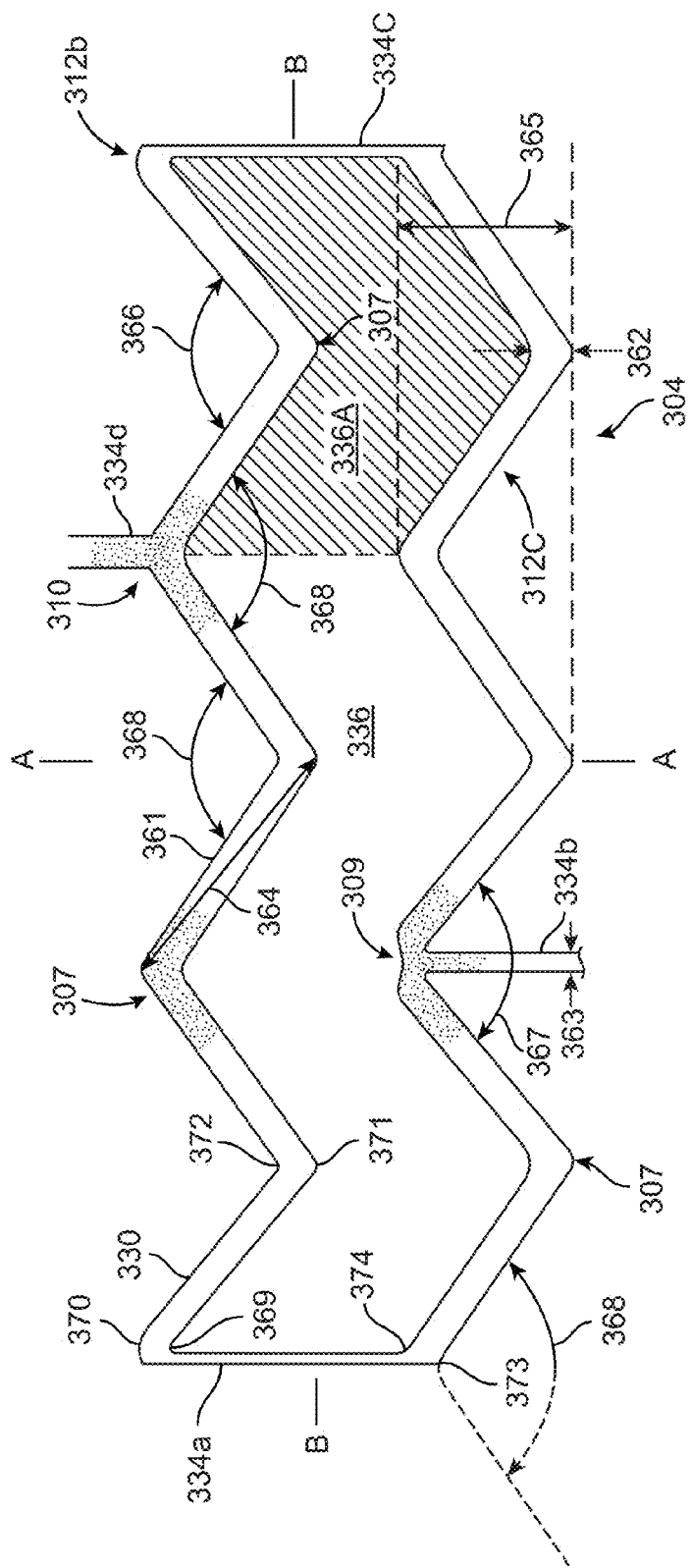
FIG. 6A is a planar view of a portion of the scaffold pattern of FIG. 5 taken at section VA-VA.
Figure 6B:
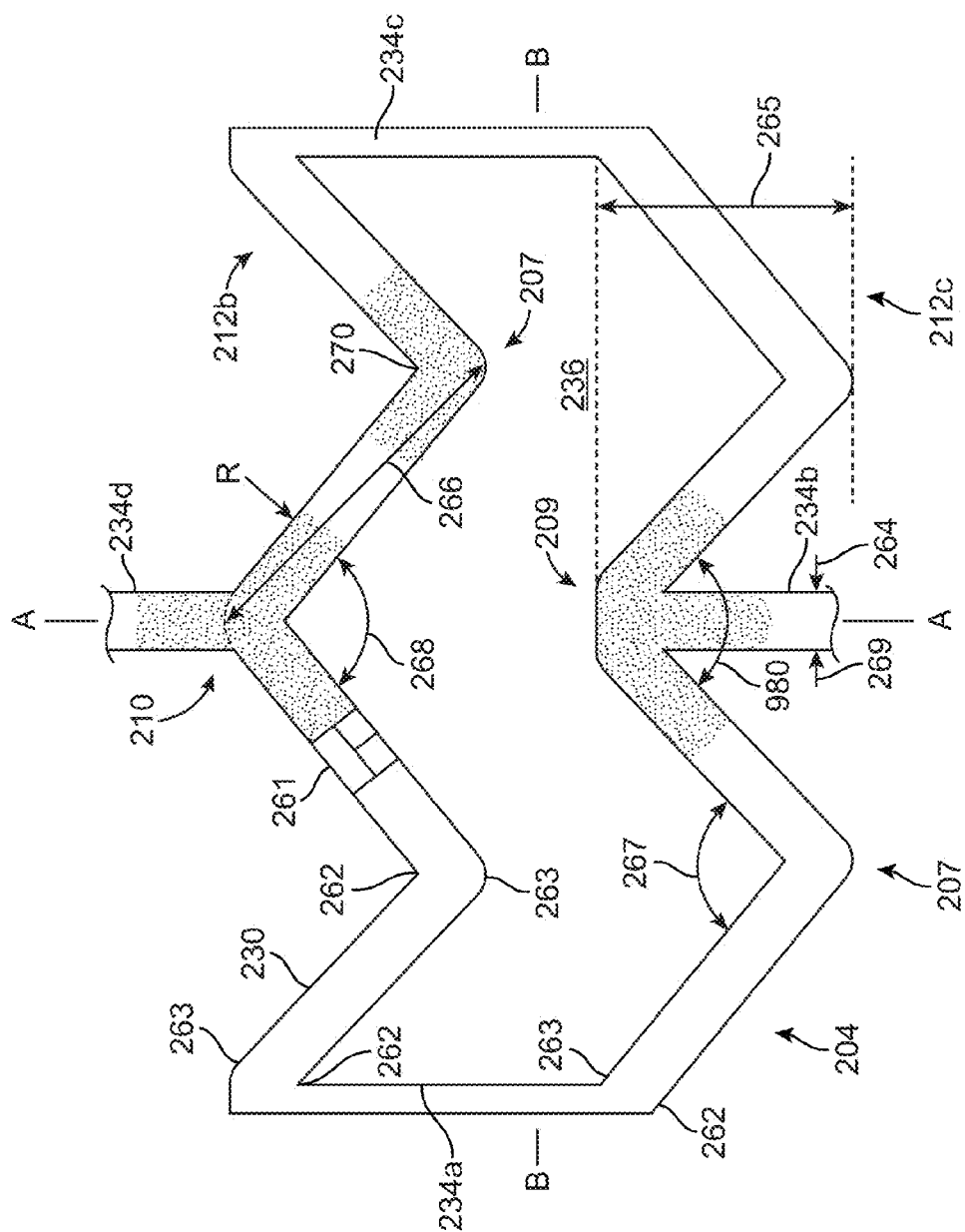
FIG. 6B is a planar view of a portion of the scaffold pattern of FIG. 3 taken at section VB-VB.

FIGS. 6A and 6B depict aspects of the repeating pattern of closed cell elements associated with each of the patterns 300 and 200, respectively. FIG. 6A shows the portion of pattern 300 bounded by the phantom box VA and FIG. 6B shows the portion of pattern 200 bounded by the phantom box VB. Therein are shown cell 304 and cell 204, respectively. In FIGS. 6A, 6B the vertical axis reference is indicated by the axis B-B and the longitudinal axis A-A. There are four cells 204 formed by each pair of rings 212 in pattern 200, e.g., four cells 204 are formed by rings 212b and 212c and the links 234 connecting this ring pair, another four cells 204 are formed by rings 212a and 212b and the links connecting this ring pair, etc. In contrast, there are three cells 304 formed by a ring pair and their connecting links in pattern 300.

Referring to FIG. 6A, the space 336 and 336a of cell 304 is bounded by the longitudinally spaced rings 312b and 312c portions shown, and the circumferentially spaced and parallel links 334a and 334c connecting rings 312b and 312c. Links 334b and 334d connect the cell 304 to the right and left adjacent ring in FIG. 4, respectively. Link 334b connects to cell 304 at a W-crown 309. Link 334d connects to cell 304 at a Y-crown 310. A "Y-crown" refers to a crown where the angle extending between a strut 330 and the link 336 at the crown 310 is an obtuse angle (greater than 90 degrees). A "W-crown" refers to a crown where the angle extending between a strut 330 and the link 334 at the crown 309 is an acute angle (less than 90 degrees). The same definitions for Y-crown and W-crown also apply to the cell 204. There are eight connected or free crowns 307 for cell 304, which may be understood as eight crowns devoid of a link 334 connected at the crown. There are one or three free crowns between a Y-crown and W-crown for the cell 304.

Additional aspects of the cell 304 of FIG. 6A include angles for the respective crowns 307, 309 and 310. Those angles, which are in general not equal to each other (see e.g., FIG. 7A for the "V2" and "V23" embodiments of scaffold having the pattern 300), are indentified in FIG. 5A as angles 366, 367 and 368, respectively associated with crowns 307, 309 and 310. For the scaffold having the pattern 300 the struts 330 have strut widths 361 and strut lengths 364, the crowns 307, 309, 310 have crown widths 362, and the links 334 have link widths 363. Each of the rings 312 has a ring height 365. The radii at the crowns are, in general, not equal to each other. The radii of the crowns are identified in FIG. 6A as radii 369, 370, 371, 372, 373 and 374.

Cell 304 may be thought of as a W-V closed cell element. The "V" portion refers to the shaded area 336a that resembles the letter "V" in FIG. 7A. The remaining un-shaded portion 336, i.e., the "W" portion, resembles the letter "W".

Referring to FIG. 6B, the space 236 of cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 3, respectively. Link 234b connects to cell 236 at a W-crown 209. Link 234d connects to cell 236 at a Y-crown 210. There are four crowns 207 for cell 204, which may be understood as four crowns devoid of a link 234 connected at the crown. There is only one free crown between each Y-crown and W-crown for the cell 204.

Additional aspects of the cell 204 of FIG. 6B include angles for the respective crowns 207, 209 and 210. Those angles, which are in general not equal to each other (see e.g., FIG. 7B for the "V59" embodiment of a scaffold having the pattern 200), are indentified in FIG. 5B as angles 267, 269 and 268, respectively associated with crowns 207, 209 and 210. For the scaffold having the pattern 200 the struts 230 have strut widths 261 and strut lengths 266, the crowns 207, 209, 210 have crown widths 270, and the links 234 have link widths 261. Each of the rings 212 has a ring height 265. The radii at the crowns are, in general, not equal to each other. The radii of the crowns are identified in FIG. 6A as inner radii 262 and outer radii 263.

Cell 204 may be thought of as a W closed cell element. The space 236 bounded by the cell 204 resembles the letter "W".

Comparing FIG. 6A to FIG. 6B one can appreciate that the W cell 204 is symmetric about the axes B-B and A-A whereas the W-V cell 304 is asymmetric about both of these axes. The W cell 204 is characterized as having no more than one crown 207 between links 234. Thus, a Y-crown crown or W-crown is always between each crown 207 for each closed cell of pattern 200. In this sense, pattern 200 may be understood as having repeating closed cell patterns, each having no more than one crown that is not supported by a link 234. In contrast, the W-V cell 304 has three unsupported crowns 307 between a W-crown and a Y-crown. As can be appreciated from FIG. 6A, there are three unsupported crowns 307 to the left of link 334d and three unsupported crowns 307 to the right of link 334b.

The mechanical behavior of a scaffold having a pattern 200 verses 300 differs in the following ways. These differences, along with others to be discussed later, have been observed in comparisons between the scaffold of FIGS. 7A-7B, which include in-vivo testing. In certain regards, these tests demonstrated mechanical aspects of scaffolds according to the invention that were both unexpected and contrary to conventional wisdom, such as when the conventional wisdom originated from state of the art metallic stents, or coronary scaffolds. For a particular design choice, whether driven by a clinical, production yield, and/or delivery profile requirement, therefore, the following characteristics should be kept in mind.

In general, a polymer scaffold that is crush-recoverable, possesses a desired radial stiffness and radial yield strength, fracture toughness and is capable of being crimped down to a target delivery diameter, e.g., at least about $D_{min}$, balances the three competing design attributes of radial yield strength and radial stiffness verses toughness, in-vivo performance verses compactness for delivery to a vessel site, and crush recovery verses radial yield strength and radial stiffness.

In-vivo performance verses compactness for delivery to the vessel site refers to the ability to crimp the scaffold down to the delivery diameter. The ring struts 230 connecting crowns to form the W-cell 204 are more restrained from rotating about an axis tangent to the abluminal surface (axis A-A). In the case of the W-V cell the V portion, the crown may tend to twist about the axis A-A under particular configurations due to the reduced number of connecting links 336. The ring portions can in effect "flip", which means rotate or deflects out-of-plane as a result of buckling (please note: "out-of-plane" refers to deflections outside of the arcuate, cylindrical-like surface of the scaffold; referring to FIG. 5A "out-of-plane" means a strut that deflects normal to the surface of this figure). When there is a link 234 at each of a crown or valley as in FIG. 5B, any tendency for the crown to buckle or flip is reduced because the ring struts are more restrained by the link 236. Essentially, the link serves to balance the load across a ring more evenly.

The "flipping" phenomenon for a scaffold constructed according to pattern 300 has been observed during crimping, as explained and illustrated in greater detail in U.S. application Ser. No. 12/861,719. The W-V cell 304 is devoid of a nearby link 334 at a crown 307 to restrain excessive twisting of the adjacent crown or valley. In essence, when there are two crowns 307 between a link 334 the restraint preventing flipping or buckling of the V portion of the ring depends on the buckling strength of the individual ring strut 330, i.e., the yield strength and stiffness of the polymer strut in torsion. When there is a link 234 connected to each adjacent crown/ valley (FIG. 5B), however, out of plane deflections at the crown 207 is restrained more, due to the bending stiffness added by the connected link 234, which restrains twisting at the adjacent crown 207.

A scaffold according to pattern 200 is correspondingly stiffer than a similarly constructed scaffold according to pattern 300. The scaffold according to pattern 200 will be stiffer both axially and in longitudinal bending, since there are more links 236 used. Increased stiffness may not, however, be desirable. Greater stiffness can produce greater crack formation over a less stiff scaffold. For example, the stiffness added by the additional links can induce more stress on rings interconnected by the additional links 234, especially when the scaffold is subjected to a combined bending (rings moving relative to each other) and radial compression and/or pinching (crushing). The presence of the link 234 introduces an additional load path into a ring, in addition to making the ring more stiff.

In-vivo requirements can favor a scaffold according to pattern 200, but a scaffold according to pattern 300 may be more easily crimped down to the delivery diameter. Other factors also affect the ability to crimp a scaffold. According to the disclosure, it was found that crown angles less than about 115 degrees for the pre-crimp scaffold can produce less fracture and related deployment problems (e.g., uneven folding/ unfolding of ring struts) than scaffold with higher crown angles (relative to the inflated diameter, in one case 6.5 mm). The scaffold is crimped to a balloon that can be inflated up to about 7.4 mm. Thus, when the balloon is hyper-inflated the scaffold attains about up to about a 7 mm inflated diameter. For a balloon catheter-scaffold assembly according to the disclosure the largest inflated diameter for the balloon is less than or equal to the scaffold diameter before crimping. As mentioned above, it is preferred that the maximum inflated diameter for the scaffold is less than the scaffold diameter before crimping.

During the course of designing a crush recoverable polymer scaffold having a desired crimped profile, it was found that when forming the scaffold at the 8 mm diameter it was difficult to crimp the scaffold to a desired crimped profile, e.g., to crimp the scaffold from the 8 mm diameter to about 2 mm profile, for two reasons. First, by imposing the 350-400% diameter reduction requirement, the polymer material was more susceptible to crack formation and propagation, simply due to strain levels experienced by the scaffold when subjected to this extensive diameter reduction. This concern was addressed by adjusting stiffness, e.g., reducing the strut angle, wall thickness and/or number of crowns. Additionally, the process steps used to form the tube (FIG. 1) improves the scaffold's resistance to crack formation and propagation, as explained earlier.

Second, even when the scaffold dimensions were adjusted to limit crack formation, there was the problem of limited space for scaffold within the crimped profile. Due to the mass of material associated with the crimped scaffold, the available space for compression of the rings to the desired crimped profile was not achievable without creating unacceptable yield stresses or fracture. Thus, even when a 350-400% diameter reduction was achievable without crack or deployment problems, the scaffold pattern would not allow further reduction without exceeding the range of articulation that the scaffold design would allow.

According to another aspect of the disclosure, there are modified crown designs for a scaffold intended to improve the fracture toughness and/or reduce the delivery diameter of the scaffold. It was discovered that a design change to an existing scaffold pattern that would overcome a limitation on reduced profile, and which could be implemented using a brittle polymer like PLLA of PLGA, was a significant reduction in the size of the inner radius of the crown or valley bridging the struts that form the crown/valley.

Figure 8B:
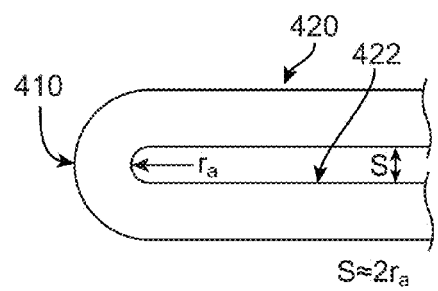

FIGS. 8A and 8B illustrate a pair of struts 420, 422 near a crown 410. In the pre-crimp state, the struts 420, 422 are separated by the crown angle $\phi$ and the crown is formed with an inner radius $r_a$. This is a typical design for a crown. The inner radius is selected to avoid stress concentrations at the crown. As the art has taught when there is a dramatic change in geometry at a hinge point, such as a crown, there is a greater likelihood cracks or yielding will form at the hinge point (thereby affecting radial yield strength) since the moment of inertia in bending across the crown is discontinuous.

In the case of a metal stent, the angle $\phi$ before crimping is less than the angle when the stent is deployed. By forming the stent with the reduced diameter, the stent may be more easily crimped to a small profile. Due to the presence of the inner radius, the angle $\phi$ is capable of being exceeded at deployment without loss of radial stiffness. If this radius is too small, however, and the strut angle at deployment exceeds the angle before crimping, i.e., $\phi$, there is a greater chance of yielding or other problems to develop due to stress concentrations at the inner radius. Due to the ductility and resiliency of metal, stents made from metal may also be crimped down further than shown in FIG. 8B. The struts 420, 422 may touch each other, i.e., S is less than $2 \times r_a$, and yet the stent can still recover and maintain its radial stiffness despite the over crimped condition.

Figure 9A:
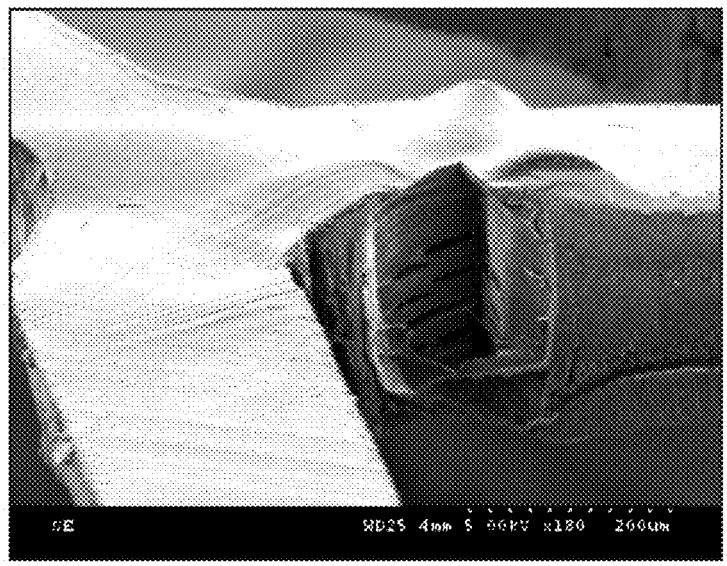
FIGS. 9A, 9F and 9G are scanning electron microscope (SEM) photographs of scaffold crowns having an inner radius substantially higher than the inner radius of the scaffold crowns in FIGS. 9B, 9C and 9D. The photographs are taken after the scaffold was expanded by a balloon.
Figure 9B:
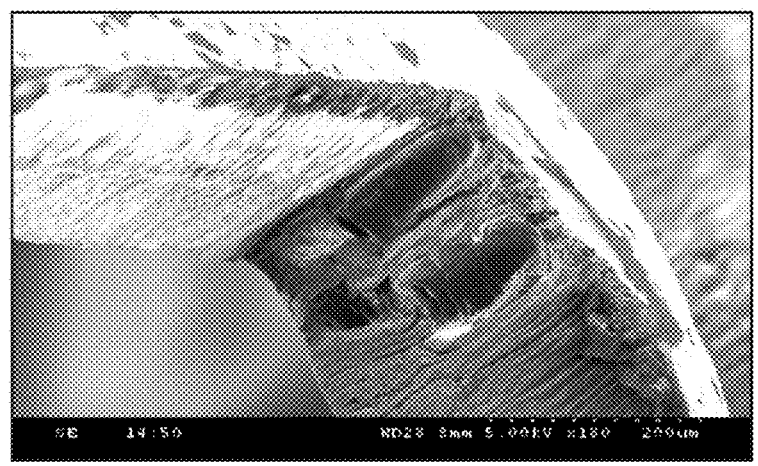
FIGS. 9B, 9C and 9D are scanning electron microscope (SEM) photographs of scaffold crowns. The crowns have an inner radius of about 0.00025 inches. The photographs are taken after the scaffold was expanded by a balloon.
Figure 9C:
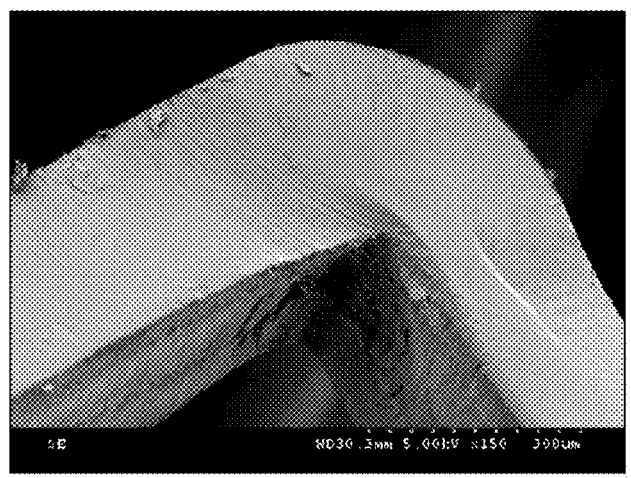
Figure 9D:
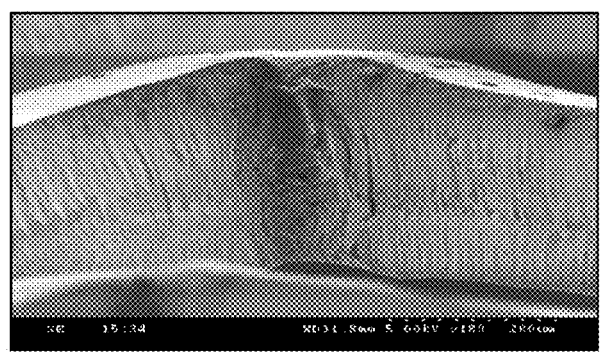
Figure 9F:
Figure 9G:

For polymer scaffold, however, it has been found that the distance S (FIG. 8B) should not generally be smaller than allowed for the radius $r_a$, i.e., S greater than or equal to $2 r_a$. For a polymer scaffold, if the struts 420, 422 are brought closer to each other, i.e., S becomes less than $2 \times r_a$, the brittleness of the material can likely result in fracture problems when the scaffold is deployed. The scaffold may not therefore be able to maintain its radial stiffness if crimped beyond the allowable distance for the radius. The scanning electron microscope (SEM) photographs included as FIGS. 9A, 9F and 9G show fractures at crowns when the distance S in FIG. 7B is less than $2 \times r_a$. As can be seen in these photographs, there is significant material failure in a W crown, free crown and Y crown.

With the objective of decreasing the distance S between struts 420, 422 (FIG. 8B) the inventors decided to reduce down the radius $r_a$ as small as possible, despite the advice offered by the art. It was discovered, to their surprise, that the scaffold was able to recover from the crimped condition to the expanded condition without significant, noticeable, reoccurring or prohibitive loss in radial yield strength. The SEMs provided as FIGS. 9B, 9C and 9D show crowns/valleys having reduced radii after being crimped, then expanded by the balloon. In these examples the crown inner radii were made as small as the cutting tool (a green light pico-second laser, described above) was able to produce. As can be seen by comparing FIGS. 9A, 9F and 9G with FIGS. 9B, 9C and 9D the scaffold having reduced radii produced some voids but there is no crack propagation. Structural integrity was maintained. The deployed scaffold in these photos maintained good radial stiffness.

Figure 8C:
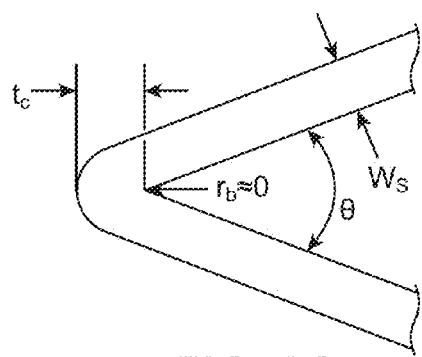
FIG. 8C-8D shows a scaffold crown formation in its expanded and crimped states for a scaffold according to the first embodiment.
Figure 8D:
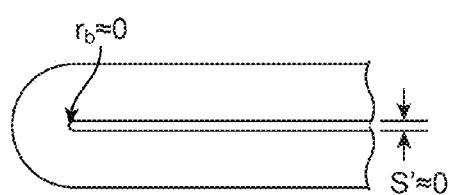

FIGS. 8C and 8D illustrate embodiments of a crown formation that produced these unexpected results. An example of a W cell having a reduced radii type of crown formation just described is illustrated in FIGS. 6B and 7B. The radius $r_b$ is about 0.00025 inches, which corresponds to the smallest radius that could be formed by the laser. The 0.00025 inch radius is not contemplated as a target radius or limit on the radius size, although it has produced the desired result for this embodiment. Rather, it is contemplated that the radius may be as close to zero as possible to achieve a reduced profile size. The radius, therefore, in the embodiments can be about 0.00025 (depending on the cutting tool), greater than this radius, or less than this radius to practice the invention in accordance with the disclosure, as will be appreciated by one of ordinary skill in the art. For instance, it is contemplated that the radii may be selected to reduce down the crimped size as desired.

An inner radius at about zero, for purposes of the disclosure, means the minimum radius possible for the tool that forms the crown structure. An inner radius in accordance with some embodiments means the radius that allows the distance S to reduce to about zero, i.e., struts are adjacent and/or touch each other as shown in FIG. 8D (S' is about, or zero).

Without wishing to be tied to a particular theory for how the scaffold according to the invention is capable of being reduced down to the theoretical minimum diameter and then expanded without loss of strength, it is believed that the selection of starting diameter being greater than the inflated diameter played a role in the favorable outcome. In contrast to the previous example where a metal stent is formed from a diameter less than its inflated diameter, which smaller diameter may be selected to facilitate a smaller crimped profile, a polymer scaffold according to preferred embodiments is formed from a starting diameter greater than the maximum inflated diameter for the balloon catheter-scaffold assembly (a larger starting diameter may be preferred to reduce acute recoil, as explained below, and/or to enhance radial yield strength characteristics in the deployed state as explained earlier in the tube processing steps for the tube of FIG. 1). As such, the strut angle pre-crimp is preferably greater than the maximum crown/strut angle when the scaffold is deployed. Stated differently, the crown angle in FIG. 8C (pre-crimp angle) is never exceeded when the balloon expands the scaffold from the crimped to deployed state. This characteristic of the crush recoverable polymer scaffold, i.e., pre-crimp crown angle greater than the deployed crown angle, is believed to provide clues as to how the polymer scaffold in the SEM photographs was able to retain radial yield strength when a minimum inner radius was used for the crown formation, contrary to the prior art. Compression, but not expansion of the scaffold when loaded by the vessel, it is believed, will not induce further weakening, despite the presence of voids. When the crown experiences only a compressive deformation relative to its pre-crimp shape (FIG. 8C), the potentially weakened area near the inner radius is subjected to only compressive stresses, which do not tend to tear the crown apart, i.e., induce crack propagation.

Crimping of the scaffold, as detailed in U.S. application Ser. No. 12/861,719, includes heating the polymer material to a temperature less then, but near to the glass transition temperature of the polymer. In one embodiment the temperature of the scaffold during crimping is raised to about 5 to 10 degrees below the glass transition temperature for PLLA. When crimped to the final, crimped diameter, the crimping jaws are held at the final crimp diameter for final dwell period. This method for crimping a polymer scaffold having crush recovery is advantageous to reduce recoil when the crimp jaws are released. Another, unexpected outcome, however, was found relating to the reduced inner radius aspect of the disclosure. It was found that during the dwell period the polymer scaffold crimped profile could be reduced to a profile less than the theoretical minimum profile.

From the example given earlier for the scaffold of FIG. 7B, the value for Dmin is 0.1048 in or 2.662 mm. When crimping this scaffold according to the crimping procedure summarized above and described in U.S. application Ser. No. 12/861,719, it was found that the scaffold could be reduced down to a crimped profile of 0.079 in or 2.0066 mm. Hence, the crimped profile was less than Dmin for this scaffold. With this profile a protective sheath of 0.085 in OD could be placed over the scaffold. When a drug coating was disposed over the scaffold, the profile of the scaffold with sheath was 0.092 in. For this scaffold the range of radial yield strength was 0.45-0.65 N/mm, range of radial stiffness was 1.00-1.20 N/mm and the crush recoverability was about 90% (50% crush).

It is believed that a reduced profile less than Dmin was achieved due to a compression of the material during the dwell period. Essentially, the pressure imposed by the crimping jaws during the dwell period at the raised temperature caused the struts forming the ring to be squeezed together to further reduced the crimped scaffold profile. According to these embodiments, the crimped scaffold having a profile less than its theoretical minimum profile was successfully deployed and tested in vivo. This scaffold possessed the desired radial stiffness properties, in addition to the desired crush recovery of above about 90% following a 50% reduction in diameter.

Figure 8E:
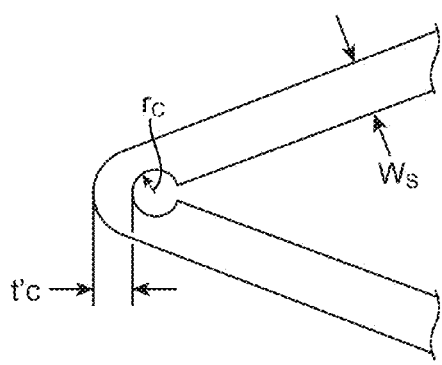
FIG. 8E-8F shows a scaffold crown formation in its expanded and crimped states for a scaffold according to an alternative embodiment.

In another aspect of this disclosure, the strut and crown formation for a crush recoverable polymer scaffold is formed to take the shape depicted in FIG. 8E, for purposes of achieving a crimped profile less than the crimped profile for the scaffold having the crown formation shown in FIG. 8A. According to these embodiments, the crown is formed with a radius $r_c$ as shown. When this scaffold is crimped, the struts may be brought close together so that the distance separating them is near zero (S" is about, or zero). In contrast to the embodiments of FIG. 8C, the radius $r_c$ is made some finite or larger radii than by forming a hole or enlarged area between the ends of the struts and crown. The thickness at the crown, $t_c'$ forming the inner radius along its inner surface may be less than the strut width (in the example of FIG. 8C the crown thickness may be larger than the strut width). This can allow a larger inner radius to be used at the crown without increasing the crimped profile.

Figure 8F:
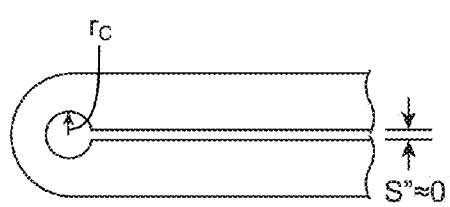

In these embodiments, a scaffold having the crown formation depicted in FIGS. 8E-8F is referred to as a "key-hole" crown formation. The name will be understood without further clarification by reference to FIG. 8F, which shows a key-hole slot or opening formed by the inner wall surfaces. In the crimped profile, the struts near the crown may be brought closer together while a hole or opening having radius $r_c$ is more or less maintained at the crown. The distance "S" is less than twice the radius $r_c$ for the "key-hole" crown formation.

Examples of scaffold embodying patterns 300 and 200 are provided in FIGS. 7A-7B (referred to as the V2 embodiment, which has a 0.008 inch wall thickness, V23 embodiments having 0.008 and 0.014 inch wall thickness and the V59 embodiment, which has a 0.011 inch wall thickness). Specific values for the various cell attributes of FIGS. 6A-6B are provided.

The scaffold V59 (pattern 200) having a pre-crimp diameter of 8 mm is capable of being crimped to a non-compliant balloon wherein the crimped profile is about 2 mm. The inflated diameter is about 6.5 mm in this example. The scaffold V2, V23 having pre-crimp diameters 7 and 9, respectively, are expanded to about 6.5 mm by a non-compliant balloon. The V2 and V23 scaffold are capable of being crimped to diameters of about 0.092 inches (2.3 mm).

According to the disclosure, it was found that the aspect ratio (AR) of a strut of a scaffold may be between about 0.8 and 1.4, the AR of a link may be between about 0.4 and 0.9, or the AR of both a link and a strut may between about 0.9 and 1.1, or about 1. Aspect ratio (AR) is defined as the ratio of width to thickness. Thus for a strut having a width of 0.0116 and a wall thickness of 0.011 the AR is 1.05.

According to the disclosure, the radial yield strength of a balloon expanded polymer scaffold having crush recoverability has a radial yield strength of greater than about 0.3 N/mm, or between about 0.32 and 0.68 N/mm, and a radial stiffness of greater than about 0.5 N/mm or between about 0.54 N/mm and 1.2 N/mm. According to the disclosure, a crush-recoverable scaffold has these ranges of stiffness and yield strength for a scaffold having a wall thickness of about 0.008 in to 0.014 in and configured for being deployed by a 6.5 mm non-compliant balloon from about a 2 mm crimped profile, or deployed to a diameter of between about 6.5 mm and 7 mm from about a 2 mm crossing profile on a balloon catheter.

A biodegradable polymer, such as PLLA (and polymers generally composed of carbon, hydrogen, oxygen, and nitrogen) is radiolucent with no radiopacity. It is desirable for a scaffold to be radiopaque, or fluoroscopically visible under x-rays, so that accurate placement within the vessel may be facilitated by real time visualization of the scaffold body, preferably the end rings. A cardiologist or interventional radiologist typically will track a delivery catheter through the patient's vasculature and precisely place the scaffold at the site of a lesion using fluoroscopy or similar x-ray visualization procedures. For a scaffold to be fluoroscopically visible it must be more absorptive of x-rays than the surrounding tissue. Radiopaque materials in a scaffold may allow for its direct visualization. One way of including these materials with a biodegradable polymer scaffold is by attaching radiopaque markers to structural elements of the scaffold, such as by using techniques discussed in U.S. application Ser. No. 11/325,973. However, in contrast to other stent or scaffold, a biodegradable, bioabsorbable, bioresorbable, or bioerodable, and peripherally implanted scaffold having crush recoverability according to the disclosure has special requirements not adequately addressed in the known art.

There is the unmet need for maintaining a desired stiffness property in the vicinity of the marker-holding material (marker structure) without increasing the minimum crimped diameter, e.g., Dmin. The marker-holding material must not interfere with the extremely-limited space available for achieving the required crossing profile or delivery diameter for the crimped scaffold on the delivery catheter, particularly in the case of a scaffold that has a diameter reduction of 300-400% or more when crimped from the starting, pre-crimp diameter to the delivery diameter, and/or where the target delivery diameter is about at most a theoretical minimum diameter (Dmin) for the scaffold. It has been found that in order to be capable of achieving a desired delivery diameter, e.g., 300-400% or more diameter reduction during crimping, the marker material (when located on a link) should not interfere with the folding of the struts forming rings of the scaffold. However, when addressing this need without consideration for the effect on radial stiffness, it was found that there was an unacceptable loss in stiffness in the vicinity of the marker structure.

Figure 10A:
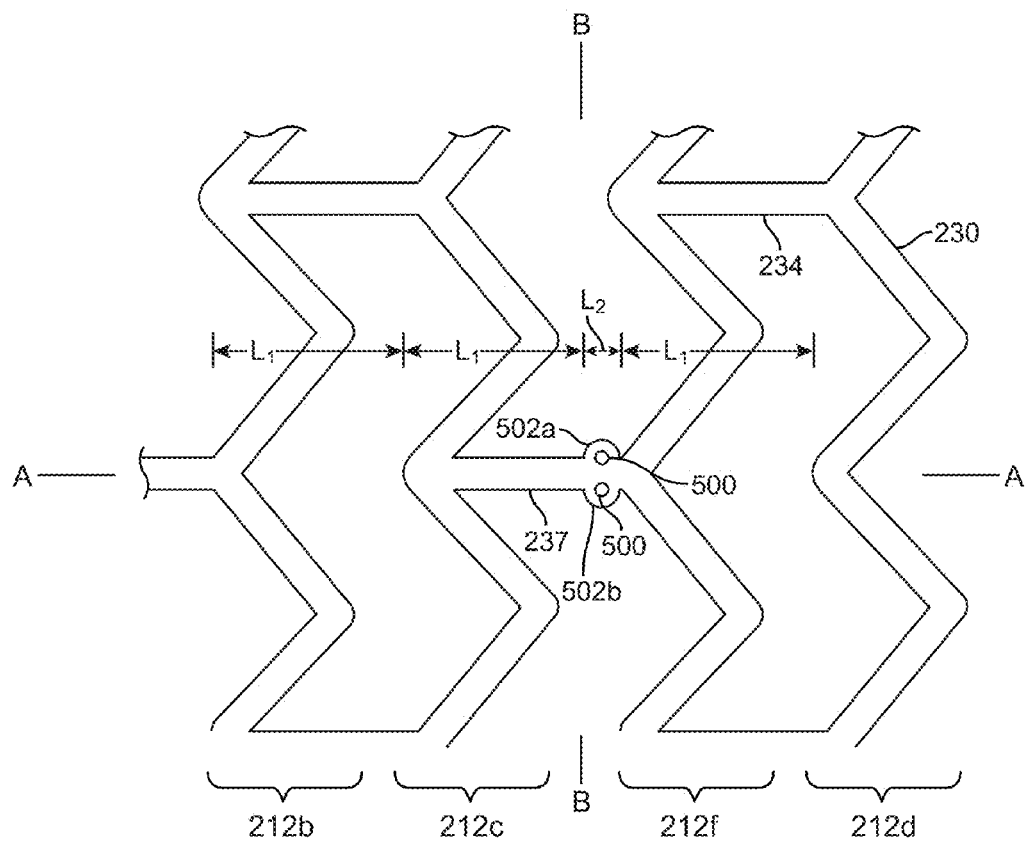
FIGS. 10A-10B show the first embodiment of a scaffold including a radiopaque marker structure formed on a link connecting rings.
Figure 10B:
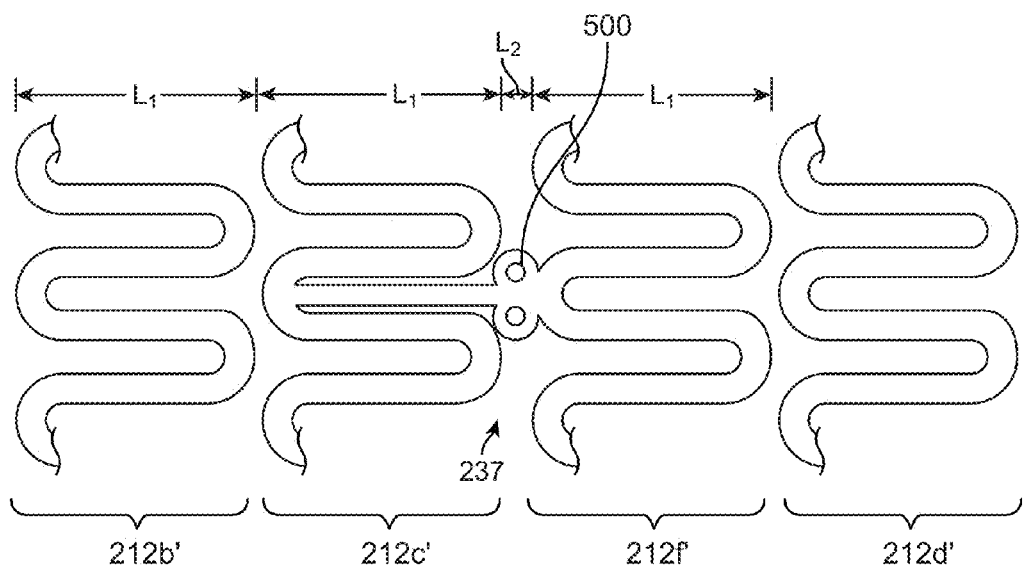

Referring to FIGS. 10A and 10B there are shown portions of the scaffold according to pattern 200. FIG. 10A shows the portion of the scaffold where the link 237 holding a radiopaque material 500 (marker 500) is located. FIG. 10B shows this same portion of the scaffold when configured in a crimped configuration. The rings 212b, 212c, 212d and 212f are shown in their compressed, folded or compact configuration as crimped rings 212b', 212c', 212d' and 212f', respectively. So that each of the rings 212 may have the same radial stiffness properties (ignoring link connections), the pair of markers 500 is preferably located on the link 237, as opposed to on a ring strut 230. In other embodiments the marker 500 may be located on the ring 212 by making suitable accommodation in the ring structure.

As can be appreciated from FIG. 10B, in order to maintain the minimum diameter, e.g., about at least the theoretical minimum crimped diameter (Dmin) for the crimped scaffold, the presence of marker structure preferably has no effect on the distance between folded struts 230. To achieve this result, the length of the link 237 may be increased, $(L_{237}=L_1+L_2,)$ over the length $L_1$ of the other links 234 that do not have the markers to carry (the length $L_2$ being about the length needed to accommodate marker structure (depots 502 and the pair of markers 500), without interfering of limiting the folding of struts 230 as necessary to achieve a 300-400% or more diameter reduction. Stents or scaffold that do not have a tight crimped diameter requirement or minimum space between structural elements of a scaffold, by contrast, may have the link connecting rings increased in size beneath the fold struts to hold a marker 500, since there remains available space for marker structure in the crimped configuration.

The depots 502 may be formed when the scaffold is cut from the tube. The depots 502 provide a hole sized slightly smaller than a diameter of a marker 500 sphere, e.g., a platinum sphere, so that the sphere may be placed in the hole and secured therein as a drug-polymer coating is applied over the scaffold. The drug-polymer coating can serve as an adhesive or barrier retaining the marker 500 within the hole of a depot 502.

In one aspect of the disclosure the diameter of a sphere forming the marker 500 necessary to achieve adequate illumination is less than the wall thickness (235, FIG. 4) of the polymer scaffold. As such, the sphere may be placed within the hole and then a coating applied over it. Since the sphere diameter is about equal to or less than the wall thickness 235 no reforming, or shaping of the sphere is necessary to achieve a flat profile. A process of applying the marker, therefore, is simplified.

When the length of a link having marker structure is increased to maintain the minimum crimped diameter according to the embodiments of FIG. 10, however, the combined radial stiffness properties of the nearby rings is reduced since they are spaced further apart. To minimize this loss in stiffness, particularly with respect to the end ring (which is inherently less stiff since it is connected to only one neighboring ring), the marker structure is located between links 212c and 212f, as opposed to rings 212d and 212f. Additionally, the marker structure is arranged so that the marker pair 500 is placed in depots 502a, 502b orientated along the vertical axis B-B as opposed to longitudinally (axis A-A). By placing the depots 502a and 502b along axis B-B the length $L_2$ is preferably less than if the markers 500 were disposed longitudinally, so that the undesirable loss in the combined radial stiffness of the adjacent rings 212c, 212f (resulting from the increased length of link 237) and the end ring 212d is minimal.

Design Process

As mentioned earlier, the problem may be stated in general terms as achieving the right balance among three competing design drivers: radial yield strength/stiffness verses toughness, in-vivo performance verses compactness for delivery to a vessel site, and crush recovery verses radial yield strength/stiffness.

Embodiments having patterns 200 or 300 were found to produce desired results with particular combinations of parameters disclosed herein, or readily reproducible in light of the disclosure. It will be recognized there were no known predecessor balloon-expandable stents having adequate crush recovery to use as a guide (indeed, the art had discouraged such a path of development for a peripheral stent). As such, various polymer scaffold combinations were fabricated based and the following properties evaluated to understand the relationships best suited to achieve the following objectives:

Crush recoverability of the scaffold without sacrificing a desired minimal radial stiffness and yield strength, recoil, deploy-ability and crimping profile;

Acute recoil at deployment—the amount of diameter reduction within ½ hour of deployment by the balloon;

Delivery/deployed profile—i.e., the amount the scaffold could be reduced in size during crimping while maintaining structural integrity;

In vitro radial yield strength and radial stiffness;

Crack formation/propagation/fracture when crimped and expanded by the balloon, or when implanted within a vessel and subjected to a combination of bending, axial crush and radial compressive loads;

Uniformity of deployment of scaffold rings when expanded by the balloon; and

Pinching/crushing stiffness.

These topics have been discussed earlier. The following provides additional examples and conclusions on the behavior of a scaffold according to the disclosure, so as to gain additional insight into aspects of the disclosed embodiments.

A scaffold fabricated with a pattern similar to pattern 300 (FIG. 5) possessed a good amount of crush recoverability, however, this scaffold's other properties were not ideal due to memory in the material following balloon expansion. The scaffold, which was initially formed from a 6.5 mm tube and deployed to about the same diameter, had acute recoil problems—after deployment to 6.5 mm it recoiled to about a 5.8 mm diameter. The scaffold also exhibited problems during deployment, such as irregular expansion of scaffold rings.

One attempt at solving the design problem proceeded in the following manner. The scaffold's properties were altered to address stiffness, yield strength, structural integrity, deployment and recoil problems while maintaining the desired crush recoverability. Ultimately, a scaffold was designed (in accordance with the disclosure) having the desired set of scaffold properties while maintaining good crush recovery properties after a 50% pinch deformation, which refers to the scaffold's ability to recover its outer diameter sufficiently, e.g., to about 90-95%, following a crushing load that depresses the scaffold to a height about equal to 50% of its un-deformed height.

The pinching stiffness (as opposed to the radial stiffness) is most influenced or most sensitive to changes in the wall thickness of the scaffold. As the wall thickness increases, the pinching stiffness increases. Moreover, the crush recoverability of a scaffold is most affected by the stresses created at the regions that deflect most outward in response to the applied load. As explained below, as the wall thickness is increased, the crush recoverability decreases due to an increased concentration of strain energy at the outwardly deflected ends of the scaffold. A design for a crush recoverable scaffold, therefore, must balance the wall thickness for increased pinching stiffness against the reduction in crush recoverability resulting from an increased pinching stiffness. Similarly, although radial stiffness is less affected by changes in wall thickness (since loads are more predominantly in-plane loading as opposed to out of plane during pinching) when wall thickness is altered to affect crush recoverability the radial stiffness must be taken into consideration. Radial stiffness changes when the wall thickness changes.

Figure 11A:
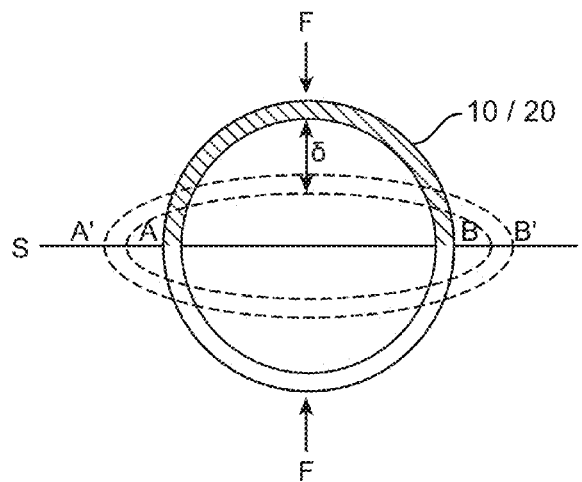
FIGS. 11A, 11B and 11C are diagrams describing a relationship between crush recoverability and wall thickness for a scaffold.
Figure 11B:
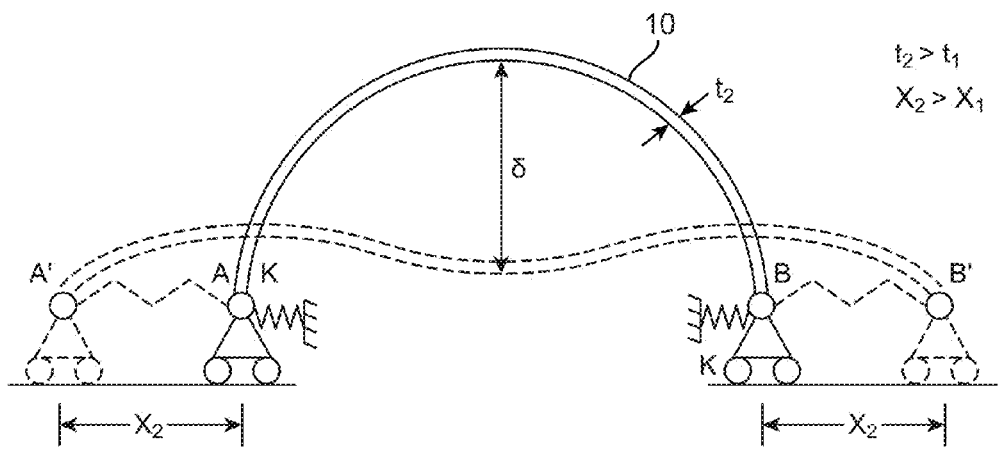
Figure 11C:
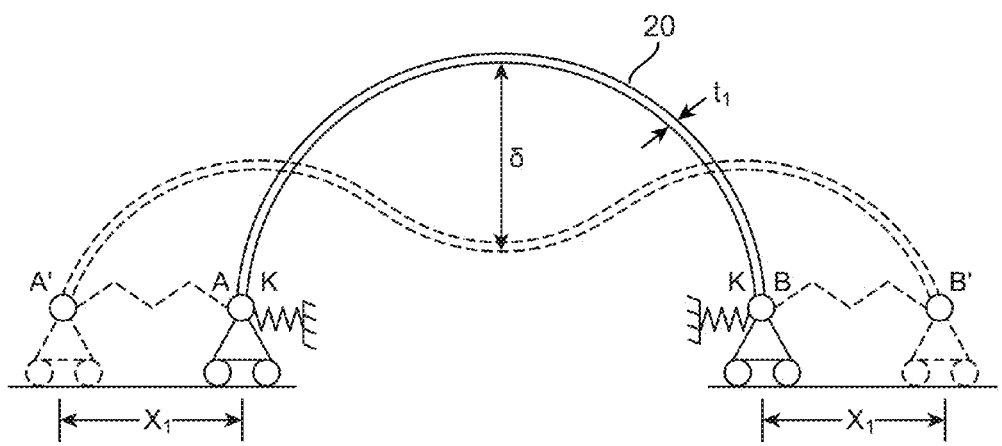

The diagrams drawn in FIGS. 11A, 11B and 11C are offered to assist with explaining a relationship between wall thicknesses and crush recoverability. FIG. 11A shows a cross-section of a scaffold in its un-deformed (unloaded) state and deformed state when subjected to a pinching load (drawn in phantom). The ends of the scaffold designated by "S" and "S'" refer to regions with the highest strain energy, as one can appreciate by the high degree of curvature in these areas when the scaffold is under the pinching load. If the scaffold will not recover or have reduction in recovery from the pinching load (F), it will be because in these regions the material has yielded which precludes or reduces recovery back to the pre-crush diameter. The equal and opposite crushing forces in force F in FIG. 11A deflect the scaffold height from its un-deformed height, i.e., the scaffold diameter, to a deformed height as indicated by δ. The region of the scaffold that will contain the highest degree of strain energy when the crushing force F is being applied is near the axis of symmetry for the deformed shape, which is shown in phantom. In the following discussion, the load reaction or material stress/strain state at the scaffold regions S and S' will be expressed in terms of the strain energy.

FIGS. 11B and 11C are simplified models of the loaded structure intended to illustrate the effects on the strain energy in region S when the scaffold has different wall thickness. Essentially, the model attempts to exploit the symmetry of the deformed shape in FIG. 11A to construct a linear stress-strain representation at region S in terms of a spring having a spring constant K. Accordingly, the scaffold properties are modeled as arcs 10/20 (½ of a hoop or ring) or half-cylinder shells supported at the ends. The arc cannot displace downward (Y-direction) when the enforced displacement δ is applied, which is believed acceptable as a boundary condition due to the symmetry in FIG. 11A. Movement in the x-direction is restrained by the spring having spring constant K. The hemispherical arc 10 in FIG. 11C has a thickness $t_1$ and the hemispherical arc 20 in FIG. 11B has a thickness of $t_2 \gg t_1$.

As the pinching load is applied in FIGS. 11B and 11C, the arcs 10 and 20 are deformed (as shown in phantom). This is modeled by an enforced displacement of the arcs 10/20 at their center by about the amount delta (δ) as in FIG. 11A. The arc 10 deforms less than arc 20, however, in terms of its curvature when the enforced displacement is applied, because its flexural rigidity is higher than arc 20. Since the curvature is less changed in arc 10, more of the % strain energy resulting from the enforced displacement will be carried by the spring at the ends, where the spring force is restraining outward movement at S. For arc 20 more % strain energy is carried in the arc, as the greater changes of curvature are intended to show, as opposed to the spring restraining movement at the ends.

Consequently, for a given applied force the % strain energy at the ends will be greater for arc 10, since the flexural rigidity of the arc 10 is greater than the arc 20. This is depicted by the displacement of the spring ($x_2 > x_1$). The % strain energy in the spring restraining arc 20 (i.e., $\frac{1}{2} K(x_2)^2$/(total strain energy in arc 20)×100) is greater than the % strain energy in the arc 10 restraining spring (i.e., $\frac{1}{2} K(x_1)^2$/(total strain energy in arc 10)×100). From this example, therefore, one can gain a basic appreciation for the relationship between wall thicknesses and crush recoverability.

In a preferred embodiment it was found that for a 9 mm scaffold pre-crimp diameter a wall thickness of between 0.008 in and 0.014 in, or more narrowly 0.008 in and 0.011 in provided the desired pinching stiffness while retaining 50% crush recoverability. More generally, it was found that a ratio of pre-crimp or tube diameter to wall thickness of between about 30 and 60, or between about 20 and 45 provided 50% crush recoverability while exhibiting a satisfactory pinching stiffness and radial stiffness. And in some embodiments it was found that a ratio of inflated diameter to wall thickness of between about 25 and 50, or between about 20 and 35 provided 50% crush recoverability while exhibiting a satisfactory pinching stiffness and radial stiffness.

Wall thickness increases for increasing pinching stiffness may also be limited to maintain the desired crimped profile. As the wall thickness is increased, the minimum profile of the crimped scaffold can increase. It was found, therefore, that a wall thickness may be limited both by the adverse effects it can have on crush recoverability, as just explained, as well as an undesired increase in crimped profile.

Provided below are results from various tests conducted on scaffolds and stents for purposes of measuring different mechanical properties and making comparisons between the properties of the stents and scaffolds. The stents used in the tests were the Cordis® S.M.A.R.T.® CONTROL® Iliac self-expanding stent (8×40 mm) ("Control stent") the REMEDY Stent (6×40 mm) by Igaki-Tamai ("Igaki-Tamai stent"), and the Omnilink Elite® stent (6×40 mm).

The data presented in Tables 4-5 (below) and Tables 4-6 in U.S. application Ser. No. 13/015,474 for the scaffolds V2, V23 and V59 are for scaffolds having the properties listed in Tables 7A and 7B, respectively. The scaffolds were crimped to a delivery balloon, then expanded to their inflated diameter. The crimping process is similar to that described at paragraphs [0071]-[0091] of U.S. application Ser. No. 12/861, 719.

The data presented in Tables 4-5 refer to scaffolds and stent properties after they were expanded by their delivery balloons. For each of the tests reported in Tables 2-6, unless stated otherwise the statistic is a mean value.

Table 4 presents data showing the percentage of crush recovery for various scaffold compared with other types of stents. The scaffolds and stents were crushed using a pair of opposed flat metal plates moved together to crush or pinch the stents and scaffold by the respective amounts shown in the tables. The test was conducted at 20 degrees Celsius.

Table 4 compares the crush-recoverability of the V2, V23 and V59 scaffold to the Igaki-Tamai stent and Omnilink Elite® (6 mm outer diameter and 40 mm length) balloon expandable stent. The crush period was brief (about 0 seconds).

TABLE 4

Approximate crush recovery using flat plate test at 20 Deg. Celsius (as percentage of starting diameter, measured 12 hours following crush)

| Stent/scaffold type | when crushed by an amount equal to 18% of starting diameter (18% crush) | when crushed by an amount equal to 33% of starting diameter (33% crush) | when crushed by an amount equal to 50% of starting diameter (50% crush) | when crushed by an amount equal to 65% of starting diameter (65% crush) |
|---|---|---|---|---|
| V23 (.008 in wall thickness) | 99% | 96% | 89% | 79% |
| V23 (.014 in wall thickness) | 99% | 93% | 84% | 73% |
| V59 (.011 in wall thickness) | 99% | 96% | 88% | 80% |
| Igaki-Tamai | 99% | 94% | 88% | 79% |
| Omnilink Elite [R] | 93% | 80% | 65% | 49% |

As can be seen in the results there is a dramatic difference between the V2, V23 and V59 crush recovery compared with the Omnilink Elite® coronary stent. The best results are achieved by the V23 (0.008 in wall thickness) and V59 scaffold when taking into consideration the radial yield strength and stiffness properties of these scaffold compared with the Igaki-Tamai stent (see Table 5 of U.S. application Ser. No. 13/015,474).

Table 5 compares the crush recovery behavior for a V23 scaffold with 0.008 in wall thickness (FIG. 7A) following a 50% crush. The data shows the percent crush recovery of the V23 scaffold following a brief (approximately 0 seconds), 1 minute and 5 minute crush at 50% of the starting diameter.

TABLE 5

Approximate crush recovery of V23 (.008 in wall thickness) using flat plate test at 20 Deg. Celsius (as percentage of starting diameter, measured 24 hours following crush)

| Crush duration | when crushed by an amount equal to 25% of starting diameter (25% crush) | when crushed by an amount equal to 50% of starting diameter (50% crush) |
|---|---|---|
| 0 second crush | 100% | 99% |
| 1 minute crush | 99% | 86% |
| 5 minute crush | 92% | 83% |

FIG. 13 (see U.S. application Ser. No. 13/015,474 shows the crush recovery properties for the V59 scaffold when crushed to 50% of its starting diameter over a 24 hour period following removal of the flat plates. There are three plots shown corresponding to the recovery of the scaffold following a 0 second, 1 minute and 5 minute crush duration. The scaffold diameter was measured at different time points up to 24 hours after the flat plates were withdrawn. As can be seen in these plots, most of the recovery occurs within about 5 minutes after the flat plates are withdrawn. It is contemplated, therefore, that an about 90% crush recovery is possible for longer periods of crush, e.g., 10 minutes, ½ hour or one hour, for scaffold constructed according to the disclosure.

When the pinching or crushing force is applied for only a brief period (as indicated by "0 sec hold time (50%)" in FIG. 13 of U.S. application Ser. No. 13/015,474 tests indicate a recovery to about 95-99% of its initial diameter. When the force is held for 1 minute or 5 minute, tests indicate the recoverability is less. In the example of FIG. 13, it was found that the scaffold recovered to about 90% of its initial diameter.

The 1 minute and 5 minute time periods being about the same suggests that any effects of the visco-elastic material succumbing to a plastic or irrecoverable strain when in a loaded state has mostly occurred.

In accordance with the disclosure, a crush-recoverable polymer scaffold (having adequate yield strength and stiffness properties, e.g., the stiffness and yield strength properties of the scaffold in Table 5 of U.S. application Ser. No. 13/015,474, has a greater than about 90% crush recoverability when crushed by an amount equal to about 33% of its starting diameter (33% crush), and a greater than about 80% crush recoverability when crushed by an amount equal to about 50% of its starting diameter (50% crush) following an incidental crushing event (e.g., less than one minute); a crush-recoverable polymer scaffold has a greater than about 90% crush recoverability when crushed by an amount equal to about 25% of its starting diameter (25% crush), and a greater than about 80% crush recoverability when crushed by an amount equal to about 50% of its starting diameter (50% crush) for longer duration crush periods (e.g., between about 1 minute and five minutes, or longer than about 5 minutes).

An acute recoil problem was observed. In one example, a scaffold was formed from a 7 mm deformed tube having a 0.008 in wall thickness. When the scaffold was balloon deployed to 6.5 mm, the scaffold recoiled to about 5.8 mm. To address this problem, the scaffold was formed from larger tubes of 8 mm, 9 mm and 10 mm. It was found that a larger pre-crimp diameter relative to the intended inflated diameter exhibited much less recoil when deployed to 6.5 mm. It is believed that the memory of the material, formed when the deformed tube was made, reduced the acute recoil.

A starting tube diameter of 10 mm, for example, for a scaffold having a 7.4 mm inflated diameter should exhibit less recoil than, say, a 8 mm tube, however, this larger diameter size introduced other problems which discouraged the use of a larger tube size. Due to the larger diameter it became difficult, if not infeasible to reduce the diameter during crimping to the desired crimped diameter of about 2 mm. Since there is more material and a greater diameter reduction, there is less space available to reduce the diameter. As such, when the starting diameter exceeds a threshold, it becomes infeasible to maintain the desired crimped profile. It was found that a 9 mm tube size produced acceptable results in that there was less recoil and a crimped profile of about 2 mm could still be obtained.

An excessive starting diameter can introduce other problems during deployment. First, when the diameter reduction from starting diameter to crimped diameter is too great, the local stresses in the scaffold hinge elements, crowns or troughs correspondingly increase. Since the polymer material tends to be brittle, the concern is with cracking or fracture of struts if stress levels are excessive. It was found that the diameter 9 mm starting diameter scaffold (in combination with other scaffold dimensions) could be reduced down to 2 mm then expanded to the 7.4 mm inflated diameter without excessive cracking or fracture.

As discussed earlier, unlike a metal stent, a design for a polymer scaffold must take into consideration its fracture toughness both during crimping and when implanted within a vessel. For a scaffold located within a peripheral artery the types of loading encountered are in general more severe in terms of bending and axial loading than a coronary scaffold, in addition to the pinching or crush forces experienced by the scaffold, due to the scaffold's proximity to the surface of the skin, and/or its location within or near an appendage of the body. See e.g. Nikanorov, Alexander, M. D. et al., *Assessment of self-expanding Nitinol stent deformation after chronic implantation into the superficial femoral artery.*

As is known in the art, a scaffold designed to have increased radial stiffness and yield strength properties does not, generally speaking, also exhibit the fracture toughness needed for maintaining structural integrity. The need to have a peripherally implanted polymer scaffold with adequate fracture toughness refers both to the need to sustain relatively high degrees of strain in or between struts and links of the scaffold and to sustain repeated, cyclical loading events over a period of time, which refers to fatigue failure.

The methods of manufacture, discussed earlier, of the tube from which the scaffold is formed are intended to increase the inherent fracture toughness of the scaffold material. Additional measures may, however, be employed to reduce instances of fracture or crack propagation within the scaffold by reducing the stiffness of the scaffold in the links, or by adding additional hinge points or crown elements to the ring. Alternatively or in addition, pre-designated fracture points can be formed into the scaffold to prevent fracture or cracks from propagating in the more critical areas of the scaffold.

Cracking/fracture problems are also observed as a consequence of irregular crimping and/or deployment of the scaffold. Irregular deployment is problematic, not only from the viewpoint of the scaffold not being able to provide a uniform radial support for a vessel, but also from the viewpoint of crack propagation, fracture and yielding of structure resulting in loss of yield strength and/or stiffness in vivo. Examples of irregular deployment include crowns being expanded beyond their design angles and in extreme cases, flipping or buckling of crowns during deployment or crimping. These problems were observed during crimping process and during deployment, examples of which are described in greater detail in U.S. application Ser. No. 12/861,719.

Pattern 300 may be susceptible to more of these types of problems than pattern 200. The links of the pattern provide less support for the ring struts forming the V segment of the W-V closed cell 304, as compared to pattern 200. It is believed that the w-shaped closed cell 204 was more capable of deploying without irregularities, such as flipping, due to its symmetry. The asymmetric loading inherent in the W-V cell 304 was more susceptible to buckling problems during crimping or deployment. These potential problems, however, should they arise, may be addressed by adopting modifications to the crimping process.

For example, a scaffold having a diameter of 7 mm and asymmetric closed cells (pattern 300) was crimped then deployed without any flipping of struts observed. A second scaffold of 9 mm diameter was then crimped to a balloon and deployed. This scaffold had the same pattern 300 as the 7 mm scaffold. The strut or crown angle was increased by the ratio of the diameters, i.e., increased by a factor of 9/7, to compensate for the change in radial stiffness resulting from the increased diameter. When the 9 mm scaffold was crimped, however, flipping occurred in the scaffold struts (primarily in the V section of the W-V closed cell). To correct this problem the W closed cell (pattern 200) was tested. This modification helped to reduce instances of flipped struts. Surprisingly, the same irregular crimping/deployment problems have not been observed for the comparable metal stent having a W-V closed cell pattern. It was concluded, therefore, that the flipping problem (in particular) is a phenomenon unique to a polymer scaffold.

To avoid flipping phenomena, should it occur in a metal stent, one might consider simply adjusting the moment of inertia of a strut to prevent out of plane (outside of the arcuate, abluminal surface) deflection of a strut. However, as noted earlier, the polymer material introduces degrees of freedom or limitations that are not present with a metallic material. In the case of minimizing undesired motion of a strut by modifying bending inertia properties of the strut one needs to be mindful that polymer struts must, generally speaking, be thicker and/or wider than the equivalent metal strut. This means there is less space available between adjacent struts and already higher wall thicknesses than the metal counterpart. This problem of space is further compounded for embodiments that form a polymer scaffold from a tube that is the formed at the deployed, or larger than deployed size for the scaffold. It is desirable to have the scaffold reduced in diameter during crimping for passage to the same vessel sites as in the case of the metal stent. Thus, the delivery profile for the crimped scaffold should be about the same as the metal stent.

A metal balloon expandable stent may be cut from a tube that is between the deployed and crimped diameters. As such, the spacing between struts is greater and the stent is more easily compressed on the balloon because the stent pre-crimp has a diameter closer to the crimped diameter. A polymer scaffold, in contrast, may be cut from a diameter tube equal to or greater than the deployed state. This means there is more volume of material that must be packed into the delivery profile for a polymer scaffold. A polymer scaffold, therefore, has more restraints imposed on it, driven by the crimped profile and starting tube diameter, that limits design options on strut width or thickness.

A well known design requirement for a vessel supporting prosthesis, whether a stent or scaffold, is its ability to maintain a desired lumen diameter due to the inward radial forces of the lumen walls including the expected in vivo radial forces imparted by contractions of the blood vessel. Referring to the examples in FIGS. 7A-7B, the radial stiffness and radial yield strength of the scaffold is influenced by the width of struts, crown radii and angles, length of ring struts extending between crowns and valleys, the number of crowns and the wall thickness (thickness 235, FIG. 4) of the scaffold. The latter parameter (wall thickness) influences the pinching stiffness, as explained earlier. During the design process, therefore, this parameter was altered to affect pinching stiffness and crush recoverability, although it also has an effect on radial stiffness. In order to affect the radial stiffness, one or more of the foregoing parameters (crown angle, crown radius, ring strut length, crown number, and strut width) may be varied to increase or decrease the radial stiffness.

To take one example, when it was found that a 7 mm scaffold's recoil problem could be overcome by increasing the starting tube diameter to 8 mm, 9 mm or perhaps even 10 mm, an initial approximation to the corresponding changes to the scaffold pattern dimensions involved increasing characteristics such as ring strut length, crown angle and link by the ratio of the diameters, e.g., 8/7 when increasing OD from 7 mm to 8 mm. However, this rough approximation was found to be insufficient in retaining other desired properties, such as crush recoverability. Thus, further refinements were needed.

The relationships between radial stiffness and above mentioned parameters are well known. However, the relationship of these stiffness-altering parameters to crush recoverability of a balloon expandable stent, much less a balloon expandable scaffold is not well known, if known at all in the existing art. Accordingly, the design process required the constant comparison or evaluation among radial stiffness, pinching stiffness and crush recoverability (assuming the changes did not also introduce yield or fracture problems during crimping and deployment) when the stiffness parameters were altered to determine whether these and related scaffold properties could be improved upon without significant adverse effects to crush recoverability.

Tables 4-6 and the accompanying text of U.S. application Ser. No. 13/015,474 provide values for acute recoil, radial yield strength and stiffness and pinching stiffness for scaffold produced by the processes of the invention, which are considered part of this disclosure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for making a medical device, comprising:
   forming a scaffold from a tube made from a polymer having a glass transition temperature (Tg);
   crimping the scaffold to a balloon at a crimping temperature between about 1 to 20 degrees less than Tg, wherein the scaffold is plastically deformed to have a crimped state; and
   fitting a removable sheath over the scaffold and balloon following crimping to limit recoil of the crimped scaffold;
   wherein the scaffold has an expanded diameter when plastically deformed from the crimped state by the balloon; and
   wherein the scaffold attains greater than 90% of the expanded diameter after being crushed by an amount equal to at least 33% of the expanded diameter.

2. The method of claim 1, wherein the polymer tube is formed from a precursor biaxially expanded at a temperature of between 20 and 50 Deg. Celsius above Tg.

3. The method of claim 1, wherein the polymer is poly (L-lactide) (PLLA), a polymer made from at least 80% L-lactide, a blockcopolymer with a PLLA block, or a copolymer of PLLA.

4. The method of claim 1, wherein the crimping step reduces the diameter of the scaffold by a factor of 2:1, 3:1 or more than 3:1.

5. The method of claim 1, wherein the scaffold is crimped to a balloon of a balloon-catheter having a distal end, wherein the sheath includes a distal end that extends beyond the catheter distal end, and wherein the sheath includes flaps that are folded to enable the flaps to be gripped and pulled to remove the sheath from the scaffold.

6. The method of claim 1, wherein the scaffold is capable of regaining more than 90% of the expanded diameter after being crushed to about 50% of the expanded diameter.

7. The method of claim 1, wherein the scaffold exhibits the more than 90% of the expanded diameter when crushed to the at least 33% of the expanded diameter using a pair of opposed flat metal plates and while the scaffold has a temperature of 20 degrees Celsius, and the scaffold diameter is measured after a crush period of about 0 seconds, 1 minute or 5 minutes.

8. The method of claim 1, wherein the crimping temperature is between 44 and 52 Degrees Celsius.

9. A method for making a medical device, comprising:
   forming a tube from a polymer, the tube having a tube diameter and a wall thickness such that a ratio of the tube diameter to the wall thickness is between 30 and 60 or between 20 and 45;
   forming a scaffold from the tube, the scaffold having a diameter, wherein the scaffold is capable of regaining more than 90% of the scaffold diameter after being crushed by an amount equal to at least 33% the scaffold diameter; and crimping the scaffold to a balloon, including the step of using a crimping temperature between 1 and 20 degrees less than a glass transition temperature of the polymer.

10. The method of claim 9, wherein the scaffold includes rings having crowns and the crowns form crown angles, wherein during crimping a ring is reduced in diameter by plastic deformation resulting in an articulation of struts about crowns; and wherein prior to crimping
the scaffold has an outer diameter of 8 to 10 mm, the crown angles for the rings are between 90 and 115 degrees, and the scaffold has a wall thickness of at least 0.008 in.

11. The method of claim 10, further including after forming the scaffold from the tube elevating the temperature of the scaffold to about 47 Degrees Celsius for a period of about 1 to 3 weeks.

12. The method of claim 9, wherein the tube is made from a polymer comprising a copolymer of poly (L-lactide) (PLLA) and polycaprolactone (PCL).

13. The method of claim 9, wherein the crimping temperature is between 44 and 52 Degrees Celsius.

14. A method for making a medical device, comprising:
forming a polymer tube having a tube diameter and a wall thickness such that a ratio of the tube diameter to the wall thickness is between 30 and 60 or between 20 and 45; and forming a scaffold from the tube, the scaffold having a diameter;

wherein the scaffold is capable of regaining more than 90% of the scaffold diameter after being crushed by an amount equal to at least 33% the scaffold diameter;

wherein the scaffold exhibits the more than 90% of the expanded diameter when crushed to the at least 33% of the expanded diameter using a pair of opposed flat metal plates and while the scaffold has a temperature of 20 degrees Celsius, and the scaffold diameter is measured after a crush period of about 0 seconds, 1 minute or 5 minutes.

15. The method of claim 14, wherein the tube has a crystallinity of between about 30% and 40%.

16. The method of claim 14, wherein the tube is made from a polymer comprising a copolymer of poly (L-lactide) (PLLA) and polycaprolactone (PCL).

17. The method of claim 14, wherein the scaffold has a network of interconnected elements including struts joined at crowns to form rings and links connecting the rings, and wherein an aspect ratio (AR) of a width to a wall thickness of a strut or link is between 0.4 and 1.4.

18. The method of claim 17, wherein the AR is between 0.4 and 0.9, the scaffold wall thickness is between about 0.008 inches and 0.014 inches and the diameter is between about 5 mm and 8 mm.

19. The method of claim 17, wherein the AR is between 0.8 and 1.4, a scaffold wall thickness is between 0.008 inches and 0.014 inches and the scaffold diameter is between 5 mm and 8 mm.

* * * * *